US007329733B2

(12) United States Patent
Côté et al.

(10) Patent No.: US 7,329,733 B2
(45) Date of Patent: Feb. 12, 2008

(54) *BACILLUS THURINGIENSIS* STRAIN, CRYSTAL GENE AND CRYSTAL PROTEIN AND USES THEREOF

(75) Inventors: Jean-Charles Côté, St-Jean-sur-Richelieu (CA); Yong-Chul Jung, Gainesville, FL (US); Eiichi Mizuki, Fukuoka (JP); Tetsuyuki Akao, Fukuoka (JP)

(73) Assignee: Agriculture Agroalimentaire Canada, St-Jean-Sur-Richelieu, Quebec (CA)

( * ) Notice: Subject to any disclaimer, the term of this patent is extended or adjusted under 35 U.S.C. 154(b) by 0 days.

(21) Appl. No.: 10/756,778

(22) Filed: Jan. 14, 2004

(65) Prior Publication Data

US 2005/0089959 A1 Apr. 28, 2005

Related U.S. Application Data

(60) Provisional application No. 60/448,883, filed on Feb. 24, 2003.

(51) Int. Cl.
*C07K 1/00* (2006.01)

(52) U.S. Cl. .................................................... 530/350

(58) Field of Classification Search ................. 530/350
See application file for complete search history.

(56) References Cited

OTHER PUBLICATIONS

GenCore, version 5.1.6; Jung Y.C, Cote J.C. Result 1 (pp. 1-2).*
GenCore version 5.1.6, pp. 1-10.*
Mizuki et al., Parasporin, a Human leukemic cell-Recognizing Parasporal Protein of *Bacillus thuringiensis*, Clinical and Diagnostic laboratory Immunology, Jul. 2000, p. 625-634.*
Arthur I. Aronson (1993): The two faces of *Bacillus thuriengiensis*: insecticidal proteins and post-exponential survival; Molecular Microbiology 7(4): 489-496.
James A. Baum et al. (1995); Regulation of insecticidal crystal protein production in *Bacillus thuriengiensis*; Molecular Microbiology 18(1) :1-12.
Christian Behl et al. (1992); Vitamin E Protect Nerve Cells from amyloid β Protein Toxicity; Biochemical and Biophysical Research Communications, vol. 186, No. 2: 944-950.
Terry J. Beveridge et al. (1994); Electron Microscopy (Chapter 3); Methods for general and molecular bacteriology pp. 41-71.
H.C. Biornboim et al. (1979); A rapid alkaline extraction procedure for screening recombinant plasmid DNA; Nucleic Acids Research, vol. 7 No. 6: 1513-1522.
N. Crickmore et al. (1998) Revision of the Nomenclature for the *Bacillus thuringiensis* Pesticidal Crystal Proteins; Microbiology and Molecular Biology Reviews, vol. 62:807-813: pp. 1-8.
Crickmore, N. et al., Revision of the Nomenclature for the *Bacillus thuringiensis* Pesticidal Crystal Proteins, Microb. Biol. Rev. (1998) vol. 62, No. 3: pp. 807-813.
N. Crickmore et al. (1998); Revision of the Nomemclature for the *Bacillus thuriengiensis* Pesticidal Crystal Proteins; Microbiology and Molecular Biology Reviews, vol. 62, No. 3: 807-813.
H. de Barjac et al. (1990); Classification of *Bacillus thuringiensis* strains; Entomophaga 35(2): 233-240.
Jerald S. Feitelson et al. (1992); *Bacillus thuriengiensis*: Insects and Beyond; Bio/Technology, vol. 10: 271-275.
Sarjeet S. Gill et al. (1992); The mode of Action of *Bacillus thuringiensis* endotoxins; Annu. Rev. Entomol. 37: 615-636.
N.S. Goodman et al. (1967); Biphasic System for Separation of Spores and Crystals of *Bacillus thuriengiensis*; Journal of Bacteriology, vol. 94, No. 2: 485.
Peter Haima et al. (1990); Development of a β-galactosidase α-complementation system for molecular cloning in *Bacillus subtilis*; Gene 86:63-69.
Peter Heiss et al. (1997); Cytotoxic Effect of Immunoconjugate Composed of Glucose-Oxidase Coupled to an Anti-Ganglioside ($G_{D2}$) Antibody on Spheroids; Anticancer Research 17: 3177-3178.
Herman Hofte et al. (1989); Insecticidal Crystal Proteins of *Bacillus thuringiensis*; Microbiological Reviews, vol. 53, No. 2: 242-255.
Yong Chul Jung et al. (1998); Characterization of a New *Bacillus thuringiensis* Subsp. *Higo* Strain Isolated from Rice Bran in Korea; Journal of Invertebrate Pathology 71: 95-96.
Ho-San Kim (2000); Comparative Study of the Frequency, Flagellar Serotype, Crystal Shape, Toxicity, and *cry* Gene Contents of *Bacillus thuringiensis* from Three Environments; Current Microbioloby, vol. 41: 250-156.
U.K. Laemmli et al. (1973); Maturation of the Head of Bacteriophage T4; J. Mol. Biol. 80: 575-599.
M.-M. Lecadet et al. (1999); Updating the H-antigen classification of *Bacillus thuringiensis*; Journal of Applied Microbiology 86: 660-672.
Dae-Weon Lee et al. (2000); Noninsecticidal Parasporal Proteins of a *Bacillus thuringiensis* Serovar shandongiensis Isolate Exhibit a Preferential Cytotoxicity against Human Leukemic T Cells; Biochemical and Biophysical Research Communications 272 : 218-223.
Didier Lereclus et al. (1989); Role, Structure, and Molecular Organization of the Genes Coding for the Parasporal 6-Endotoxins of *Bacillus thuriengiensis*; Regulation of Procaryotic Development, Chapter 13; American Society of Microbiology 255-276.
Jane R. McLaughlin (1981); Unique Features in the Ribosome Binding Site Sequence of the Gram-positive *Staphylococcus aureus* β-Lactamase Gene; The Journal of Biological Chemistry, vol. 256, No. 21: 11283-11291.

(Continued)

*Primary Examiner*—Karen Cochrane Carlson
*Assistant Examiner*—Agnes B. Rooke
(74) *Attorney, Agent, or Firm*—Goudreau Gage Dubuc

(57) ABSTRACT

A novel *Bacillus thuringiensis* strain deposited at the International Depository Authority of Health Canada in Winnipeg under accession number IDAC010201-5, its crystal gene having the sequence SEQ ID NO: 1 and crystal protein encoded by same having the sequence SEQ ID NO: 2 and uses thereof. More specifically, the present invention is concerned with a novel *Bacillus thuringiensis*, novel cry31 protoxin and toxin, nucleotide sequences encoding same and anti-cancer therapeutic applications for the toxin.

5 Claims, 11 Drawing Sheets

OTHER PUBLICATIONS

E. Mizuki et al. (1999); Unique activity associated with non-insecticidal *Bacillus thuringiensis* parasporal inclusions: in vitro cell-killing action on human cancer cells; Journal of Applied Microbiology 86: 477-486.

Eiichi Mizuki et al. (2000); Parasporin, a Human leukemic Cell-Recognizing Parasporal Protein of *Bacillus thuringiensis*; Clinical and Diagnostic Laboratory Immunology, vol. 7 No. 4: 625-634.

Charles P. Moran et al. (1982); Nucleotide Sequences that Signal the Initiation of Transcription and Translation in *Bacillus subtilis*; Mol. Gen Genet 186: 339-346.

M. Ohba (1996): *Bacillus thuringiensis* populations naturally occurring on mulberry leaves: a possible source of the populations associated with silkworm-rearing insectaries; Journal of Applied Bacteriology 80: 56-64.

Michio Ohba et al. (1986); Insect Toxicity of *Bacillus thuringiensis* Isolated ffrom Soils of Japan; Journal of Invertebrate pathology 47 : 12-20.

J.Y. Roh et al. (1996); Characterization of novel non-toxic *Bacillus thuringiensis* isolates from Korea; Letters in Applied Microbiology 23 : 249-252.

H. Saitoh et al. (1998); Characterization of mosquito larvicidal parasporal inclusions of a *Bacillus thuringiensis* seroval *higo* strain; Journal of Applied Microbiology 84: 883-888.

H. Ernest Schnepf et al. (1985) The Amino Acid Sequence of a Crystal Prottein from *Bacillus thuringiensis* Deduced from the DNA Base Sequence; The Journal of Biological Chemistry, vol. 260, No. 10:6264-6272.

E.M. Southern (1975); Detection of Specific Sequences Among DNA Fragments Separated by Gel Electrophoresis; J. Mol. Biol. 98: 503-417.

D.P. Stahly et al. (1978); Possible Origin and Function of the Parasporal Crystals in *Bacillus thuringiensis*; Biochemical and Biophysical Research Communications, vol. 84, No. 3: 581-588.

Wendy E. Thomas et al. (1983); *Bacillus thuringiensis* Var Israelensis Crystal 6-Endotoxin: Effects on Insect and Mammalian Cells in vitro and in vivo; J. Cell Sci. 60: 181-197.

Ignacio Tinoco, Jun. et al. (1973); Improved Estimation of Secondary Structure in Ribonucleic Acids; Nature New Biology vol. 246:40-41.

Jari Vehmaanpera (1989); Transformation of *Bacillus amyloliquefaciens* by electroporation; Fems Microbiology Letters 61: 165-170.

Jung, Y.-C. (2001) *Bacillus thuringiensis* Strain M15, a Novel Autoagglutinable, Non-Serotypeable Strain-Cloning and Characterizaton of a Novel *cry31A*-type Crystal Protein Gene, *cry31Aa2*, and Two New Insertion Sequences, IS231M and -N. Département de sciences biologiques, Faculté des arts et des sciences, Université de Montréal.

Sambrook, J., Fritsch, E. F., and Maniatis, T. (1989). "Molecular cloning. A Laboratory manual," 2nd ed. Cold Spring Harbor Laboratory Press, Cold Spring Harbor, New York.

* cited by examiner

```
GTGGACCCATTTTCTAATTATTCTGAACAAAAATACCCAGATTCAAATAATAACCAAGAACTAATTACAGAATCCTC
TTCATTTTATTCGGATACTACTAATGAAAATATGAAAACTTACCATCCAATTGAACAAGATATTCTCAAATTTGCAA
ATCAAGAATTTCCCGATAATTATTATCAACATTCCGATGTTTCTAATTCATATCAAAATATGAAAACAGAAATCGTA
AATACAGATTTACCCTATAATACAAATAATATAAATAGTATGCGAAATACTCTATGCAGAGATTTACCTCCCGAGAC
TAACATGAGCATTTATGATAATTTACGATCTACTGTTACTGTTCCTTCATTTTCTAATCAATTTGATCCTATAAAAT
TTCTTCACGATATTGAAATTGCTATAGAAACTGGATCATTTTCTGCATTAACGCAATCTAACATGAATCAAGGTGGT
ACTGATATTGCTCCAATGTTAATCTCTACATTTTTTAAAGTTGCAGGTAGTTTACTTCCATTTCCTCTATCATCATT
AGGTGCTTTGGCTTCCTTTTATGTTACAGATTCACAAACAGGCGCTATGGCAAATTTATGGAGACAAATGGTAGATT
ATGTTGAAAAAAGAATTGATTCTAAAATATTAGATTATCATAATTTTATTATGGGAGCAGAACTCGCAGCATTAAAT
GCAAGTTTAAAAGAATACGCACGAGTAGTTAAAATTTTTGAAAATGATATGAACAGAATAGCTGAACCACCTTCAAC
TGGAGTTATCACTCAATTCAGAATTCTTAATGATAATTTCATTAAATATATTGCAAAATTACAATTCTCAACAAATC
AATCAGATTTACAATATCCTGTCCTAACTTTACCATTACGTGCACAAGCATGTGTAATGCATTTAATGTTATTAAAA
GATGCAACGACTTCTGTGTGGGGACAACAAATAGACTCGCAACAATTAAATGGGTATAAAGCAGAATTAATACGTTT
AATAAAAGTATATACTAATGATGTAAACACAACGTATAATCAAGGGCTAGAGCTAGAAAAAGCTAAACCACTAAATT
ATTCTGATCCTGAAGAATATTTACAAGCAGGACGTCCAGATATATCTGTATTACGCAGTAACTTTAAAGAGGTTATG
AAGTGGAATAAAGTAGCGAAATATAAACGTGGAATGGCTATGAGTGCTTTATCATTAGCTGCATTATTTCCAACTTT
CGGACCAAATTATCCAAAACAAGCATTAAAAGTTGTGCAATCTAGACAAATTTTTGCACCTGTAATTGGAATACCAG
GCGGTATAACAAGTCAAGATAGTGGTCCCACTTTTGGTAGTATGAGATTTGATGTAAAAACTTATGATCAAATTGAT
GCGTTACGACAACTAATGGAATTATATATTCAACCTTTAAAATCTGCTTACTTTTGGATATATGAATCGGATTGGAA
AGTTCGTGCAACTTATGTCAATGATTATATTGGTAAAAGAGGGTCAAATACAGGTGCTGCTTGGCACATGTGGTCAA
GTGATCCTTCAGCCATATACACTTCTGCACTAGGAGCAGCAGGATACGCTCCTAACGTTGTTGGTGTAAGATATTCA
CATGGGGGTAGTTACACAAAAGGTATGGCACCCGCAAATACTAATGCGTATGCTCCATTTGAATTTAAATATCCTGG
TTATAAACTACACAGTGTTAGTGCTTATGGATTAAGTAAAGCACCTGATGCAGCTGATTCTGTTATGTTTGGATTTA
GACCTGTATTGTTAGAAAATGAAGCAAATCAATTATTAACAGATACAGCATTGCAAATTCCAGCAGAAATAGGAATA
ACAGATGTCGTACCTGCATTTGGTAGAACAGAAGAACCTATTAATGGTCAAGATGCAATAAGAATATGGGAAAGTTT
TACAAGTGGATTTGGCTTTACTTATACTGTTGATTCTCCACAAAAACAAAAATATAAAATCATTTATAGAATTGCAA
ATAACTTAAGCGCTTCTACAGTTTCTTTAACCTATAATAATCAAACATTTTTTCACTGATATTTTAAATACTTCATTA
GATCCAAATGGAGTAAGAGGAAATTATGGTTCTTATACACTTGTAGAAGGTCCTATTATTGAATTTTCTCAAGGAAC
TAATATCTTTAAACTAGGATCACAAAAAGGAGAATTCGCTATAGATTCCATTATTTTTAGTCCTGTTGTTTAA
```

Cry31Aa2: 1 MDPFSNYSEQKYPDSNNNQELITESSSFYSDTTNENMKTYHPIEQDILKFANQEFPDNYY 60
Cry31Aa1: 1 *********************K**********A*N*********TSH* 60

Cry31Aa2: 61 QHSDVSNSYQNMKTEIVNTDLPYNTNNINSMRNTLCRDLPPETNMSIYDNLRSTVTVPSF 120
Cry31Aa1: 61 *****-------------------D*****K********************* 101

Cry31Aa2: 121 SNQFDPIKFLHDIEIAIETGSFSALTQSNMNQGGTDIAPMLISTFFKVAGSLLPFPLSSL 180
Cry31Aa1: 102 ***************Q***************N*******S******** 161

Cry31Aa2: 181 GALASFYVTDSQTGAMANLWRQMVDYVEKRIDSKILDYHNFIMGAELAALNASLKEYARV 240
Cry31Aa1: 162 ************************************************************ 221

Block 1

Cry31Aa2: 241 VKIFENDMNRIAEPPSTGVITQFRILNDNFIKYIAKLQFSTNQSDLQYPVLTLPLRAQAC 300
Cry31Aa1: 222 ********M*********************************************** 281

Block 1 (Continued)

Cry31Aa2: 301 VMHLMLLKDATTSVWGQQIDSQQLNGYKAELIRLIKVYTNDVNTTYNQGLELEKAKPLNY 360
Cry31Aa1: 282 ************************************************************ 341

Block 2

Cry31Aa2: 361 SDPEEYLQAGRPDISVLRSNFKEVMKWNKVAKYKRGMAMSALSLAALFPTFGPNYPKQAL 420
Cry31Aa1: 342 **************************R***************************** 401

Block 2 (Continued)

Cry31Aa2: 421 KVVQSRQIFAPVIGIPGGITSQDSGPTFGSMRFDVKTYDQIDALRQLMELYIQPLKSAYF 480
Cry31Aa1: 402 *********************HSG***************R************ 461

Cry31Aa2: 481 WIYESDWKVRATYVNDYIGKRGSNTGAAWHMWSSDPSAIYTSALGAAGYAPNVVGVRYSH 540
Cry31Aa1: 462 Y***********************LG*****V******************** 521

Block 3

Cry31Aa2: 541 GGSYTKGMAPANTNAYAPFEFKYPGYKLHSVSAYGLSKAPDAADSVMFGFRPVLLENEAN 600
Cry31Aa1: 522 ********P**************************T**************** 581

Block 3 (Continued) Block 4

Cry31Aa2: 601 QLLTDTALQIPAEIGITDVVPAFGRTEEPINGQDAIRIWESFTSGFGFTYTVDSPQKQKY 660
Cry31Aa1: 582 **********************************I********************* 641

Block 4 (Continued)

Cry31Aa2: 661 KIIYRIANNLSASTVSLTYNNQTFFTDILNTSLDPNGVRGNYGSYTLVEGPIIEFSQGTN 720
Cry31Aa1: 642 ************************************************************ 701

Block 5

Cry31Aa2: 721 IFKLGSQKGEFAIDSIIFSPVV 742
Cry31Aa1: 702 **R**************S 723

Figure 5

AAGAGAATATTCCTGTAGATATTATATTTAAATATAGTCTCACTCCTCTTGCTTATCATACCGTTGATACCAATCATGTAAAACTCAAACATATTGGATTAG 102
TCCCTTTTTCTTCTTCCGATCCTAATCTATACAGCATACAAGGTGAATTTCAATTTTTTTATGAATAAACAATACTTATGAAAAAACTATTTATAAGTATAT 204
TAAAGGACAACAAAGTGAGCATAATGATGGTTTTGATGGGAAAGAATAATAGGCTTTAGTCAATAGTGGTTCAGTTAATTATTGATATATTTTGATATTTAT 306

AATACAAACATTTCTCAAAAATTCTCCTTGCTTATGTCCATTTATACCCAAAAAAGCGAGGACAATGTATATATTTCTCTATCTATCATAGAGTAAATATAG 408
-35 -10

ACTGTATACATTTTTAGTCTTATCTTTGAGTTTTTATATATTTTAAAGTTTGTTTGATAAATTTTCAGGAAAAAAAGATCTCAACGACTTTTGTATGTCGGT 510

GARCARAARTAYCCNGAY
TGTTTACTATGTGAAAGGTGGAGATATTGTGGACCCATTTTCTAATTATTCTGAACAAAAATACCCAGATTCAAATAATAACCAAGAACTAATTACAGAATC 612
RBS M D P F S N Y S E Q K Y P D S N N N Q E L I T E S
CTCTTCATTTTATTCGGATACTACTAATGAAAATATGAAAACTTACCATCCAATTGAACAAGATATTCTCAAATTTGCAAATCAAGAATTTCCCGATAATTA 714
S S F Y S D T T N E N M K T Y H P I E Q D I L K F A N Q E F P D N Y
TTATCAACATTCCGATGTTTCTAATTCATATCAAAATATGAAAACAGAAATCGTAAATACAGATTTACCCTATAATACAAATAATATAAATAGTATGCGAAA 816
Y Q H S D V S N S Y Q N M K T E I V N T D L P Y N T N N I N S M R N
TACTCTATGCAGAGATTTACCTCCCGAGACTAACATGAGCATTTATGATAATTTACGATCTACTGTTACTGTTCCTTCATTTTCTAATCAATTTGATCCTAT 918
T L C R D L P P E T N M S I Y D N L R S T V T V P S F S N Q F D P I
AAAATTTCTTCACGATATTGAAATTGCTATAGAAACTGGATCATTTTCTGCATTAACGCAATCTAACATGAATCAAGGTGGTACTGATATTGCTCCAATGTT 1020
K F L H D I E I A I E T G S F S A L T Q S N M N Q G G T D I A P M L
AATCTCTACATTTTTTAAAGTTGCAGGTAGTTTACTTCCATTTCCTCTATCATCATTAGGTGCTTTGGCTTCCTTTTATGTTACAGATTCACAAACAGGCGC 1122
I S T F F K V A G S L L P F P L S S L G A L A S F Y V T D S Q T G A
TATGGCAAATTTATGGAGACAAATGGTAGATTATGTTGAAAAAAGAATTGATTCTAAAATATTAGATTATCATAATTTTATTATGGGAGCAGAACTCGCAGC 1224
M A N L W R Q M V D Y V E K R I D S K I L D Y H N F I M G A E L A A
ATTAAATGCAAGTTTAAAAGAATACGCACGAGTAGTTAAAATTTTTGAAAATGATATGAACAGAATAGCTGAACCACCTTCAACTGGAGTTATCACTCAATT 1326
L N A S L K E Y A R V V K I F E N D M N R I A E P P S T G V I T Q F
CAGAATTCTTAATGATAATTTCATTAAATATATTGCAAAATTACAATTCTCAACAAATCAATCAGATTTACAATATCCTGTCCTAACTTTACCATTACGTGC 1428
R I L N D N F I K Y I A K L Q F S T N Q S D L Q Y P V L T L P L R A
ACAAGCATGTGTAATGCATTTAATGTTATTAAAAGATGCAACGACTTCTGTGTGGGGACAACAAATAGACTCGCAACAATTAAATGGGTATAAAGCAGAATT 1530
Q A C V M H L M L L K D A T T S V W G Q Q I D S Q Q L N G Y K A E L
AATACGTTTAATAAAAGTATATACTAATGATGTAAACACAACGTATAATCAAGGGCTAGAGCTAGAAAAAGCTAAACCACTAAATTATTCTGATCCTGAAGA 1632
I R L I K V Y T N D V N T T Y N Q G L E L E K A K P L N Y S D P E E
ATATTTACAAGCAGGACGTCCAGATATATCTGTATTACGCAGTAACTTTAAAGAGGTTATGAAGTGGAATAAAGTAGCGAAATATAAACGTGGAATGGCTAT 1734
Y L Q A G R P D I S V L R S N F K E V M K W N K V A K Y K R G M A M
GAGTGCTTTATCATTAGCTGCATTATTTCCAACTTTCGGACCAAATTATCCAAAACAAGCATTAAAAGTTGTGCAATCTAGACAAATTTTTGCACCTGTAAT 1836
S A L S L A A L F P T F G P N Y P K Q A L K V V Q S R Q I F A P V I
TGGAATACCAGGCGGTATAACAAGTCAAGATAGTGGTCCCACTTTTGGTAGTATGAGATTTGATGTAAAAACTTATGATCAAATTGATGCGTTACGACAACT 1938
G I P G G I T S Q D S G P T F G S M R F D V K T Y D Q I D A L R Q L
AATGGAATTATATATTCAACCTTTAAAATCTGCTTACTTTTGGATATATGAATCGGATTGGAAAGTTCGTGCAACTTATGTCAATGATTATATTGGTAAAAG 2040
M E L Y I Q P L K S A Y F W I Y E S D W K V R A T Y V N D Y I G K R
AGGGTCAAATACAGGTGCTGCTTGGCACATGTGGTCAAGTGATCCTTCAGCCATATACACTTCTGCACTAGGAGCAGCAGGATACGCTCCTAACGTTGTTGG 2142
G S N T G A A W H M W S S D P S A I Y T S A L G A A G Y A P N V V G
TGTAAGATATTCACATGGGGGTAGTTACACAAAAGGTATGGCACCCGCAAATACTAATGCGTATGCTCCATTTGAATTTAAATATCCTGGTTATAAACTACA 2244
V R Y S H G G S Y T K G M A P A N T N A Y A P F E F K Y P G Y K L H
CAGTGTTAGTGCTTATGGATTAAGTAAAGCACCTGATGCAGCTGATTCTGTTATGTTTGGATTTAGACCTGTATTGTTAGAAAATGAAGCAAATCAATTATT 2346
S V S A Y G L S K A P D A A D S V M F G F R P V L L E N E A N Q L L
AACAGATACAGCATTGCAAATTCCAGCAGAAATAGGAATAACAGATGTCGTACCTGCATTTGGTAGAACAGAAGAACCTATTAATGGTCAAGATGCAATAAG 2448
T D T A L Q I P A E I G I T D V V P A F G R T E E P I N G Q D A I R
AATATGGGAAAGTTTTACAAGTGGATTTGGCTTTACTTATACTGTTGATTCTCCACAAAAACAAAAATATAAAATCATTTATAGAATTGCAAATAACTTAAG 2550
I W E S F T S G F G F T Y T V D S P Q K Q K Y K I I Y R I A N N L S
CGCTTCTACAGTTTCTTTAACCTATAATAATCAAACATTTTTCACTGATATTTTAAATACTTCATTAGATCCAAATGGAGTAAGAGGAAATTATGGTTCTTA 2652
A S T V S L T Y N N Q T F F T D I L N T S L D P N G V R G N Y G S Y
TACACTTGTAGAAGGTCCTATTATTGAATTTTCTCAAGGAACTAATATCTTTAAACTAGGATCACAAAAAGGAGAATTCGCTATAGATTCCATTATTTTTAG 2754
T L V E G P I I E F S Q G T N I F K L G S Q K G E F A I D S I I F S
TCCTGTTGTTTAATAGTGTAGTACCATTAGACCCAGACCCATGGTTTCCAGTCCAGAATATTCCCCAGATTTCATAGTATGCTTCGATCCCGCATGTTTTAT 2856
P V V ***
GTACAAACACATCCTTTTTAGATAGCATTCCAATTATAGGGATGCTCTTTTTTTGATTTCTGGCCTATCCTTCTCATTTCATAGATTTTTAATTAGTACCCT 2958

TTACAAAAAGTAAACCCACCATCTTCGAACAAATCTTTGATTTCTATTTTTAAGAATAATCAATCTGTTGAACAATTTATAATTCTTTTGAAGAGAATTTCA 3060
TTTTATTTGTTCGCTTAAGTTGATAGGCATGTGGTTCTACCCCTAATAAGTGTCACAGAACACTAATTCTAAGACATTTATCGTAAAAAAATAGTAAATTCA 3162
TACAATACAGTTAAACTTTCCTCAGTAGCTCACGTTTTTCGATTTCGGGTGTTTTTACTCATTTCCCCCTTTGTTTTTAGGAGAGAGTGCTGGCTGGGGGTT 3264
TGGGGGCTAGCCCCCAAGAACTTAACGTAACTGAATATGGAATAAGCTT 3313

Figure 9

GTGGACCCGTTTTCTAATTATTCTGAACAAAAATACCCAGATTCAAATAATAACCAAGAACTAATTACAAAATCC
TCTTCATTTTATTCGGATACTACTAATGAAAATGCAAAAAATTACCACCCAATTGAACAAGATATTCTCAAATTT
ACAAATCAAGAATTTTCCGATAATCATTATCAACATTCCGATGTTTCAAATGATATAAATAGTATGCGAAATACT
CTATGCAAAGATTTACCTCCTGAGACTAACATGAGCATTTATGATAATTTACGATCTACTGTTACTGTTCCTTCA
TTTTCTAATCAATTTGATCCTATAAAATTTCTTCACGATATTGAAATTGCTATACAAACTGGATCATTTTCTGCA
TTAACGCAATCTAACATGAATCAAGGTGGTACTGATATTAATCCAATGTTAATCTCTACATTTTTTAAAGTTGCA
AGTAGTTTACTTCCATTTCCTCTATCATCATTAGGTGCTTTAGCTTCCTTTTATGTTACAGATTCACAAACAGGC
GCTATGGCAAATTTATGGAGACAAATGGTAGATTATGTTGAAAAAAGAATTGATTCTAAAATATTAGATTATCAT
AATTTTATTATGGGAGCAGAACTCGCAGCATTAAATGCAAGTTTAAAAGAATACGCACGAGTAGTTAAAATTTTT
GAAAATGATATGAACAGAATGGCTGAACCACCTTCAACTGGAGTTATCACTCAATTCAGAATTCTTAATGATAAT
TTCATTAAATACATTGCAAAATTACAATTCTCAACAAATCAATCAGATTTACAATATCCTGTCCTAACTTTACCA
TTACGTGCACAAGCATGTGTAATGCATTTAATGTTATTAAAAGATGCAACGACTTCTGTGTGGGACAACAAATA
GACTCGCAACAATTAAATGGGTATAAAGCAGAATTAATACGTTTAATAAAAGTATATACTAATGATGTAAACACA
ACGTATAATCAAGGGCTAGAGCTAGAAAAAGCTAAACCACTAAATTATTCTGATCCTGAAGAATATTTACAAGCA
GGGCGTCCAGATATATCTGTATTACGCAGTAACTTTAAAGAGGTTATGAAGTGGAATAGAGTAGCGAAATATAAA
CGTGGAATGGCTATGAGTGCTTTATCATTAGCTGCATTATTTCCAACTTTCGGACCAAATTATCCAAAACAAGCA
TTAAAAGTTGTGCAATCTAGACAAATTTTTGCACCTGTAATTGGAATACCAGGCGGTATAACAAGTCAAGATCAT
TCTGGCACTTTTGGTAGTATGAGATTTGATGTAAAAACTTATGATCAAATTGATGCGTTACGACGACTAATGGAA
TTATATATTCAACCTTTAAAATCTGCCTACTTCTATATATATGAATCGGATTGGAAAGTTCGTGCAACTTATGTC
AATGACTATATTGGTAAAAGAGGGTCTAATACAGGTCTTGCCTGGGGAATGTGGTCAAGTGATCCTTCAGTCATA
TACACTTCTGCACTAGGAGCAGCAGGATACGCTCCTAACGTTGTTGGTGTAAGATATTCACATGGGGGTAGTTAC
ACAAAAGGTATGGCACCCCCAAATACTAATGCGTATGCTCCATTTGAATTTAAATATCCTGGTTATAAACTACAC
AGTGTTAGTGCTTATGGATTAAGTAAAGCACCTGATACAGCTGATTCTGTTATGTTTGGATTTAGACCTGTATTG
TTAGAAAATGAAGCAAATCAATTATTAACAGATACAGCATTGCAAATTCCAGCAGAAATAGGAATAACAGATGTC
GTACCTGCATTTGGTAGAACAGAAGAACCTATTAATGGTCAAGATGCAATAATAATATGGGAAAGTTTTACAAGT
GGATTTGGCTTTACTTATACTGTTGATTCTCCACAAAAACAAAAATATAAAATCATTTATAGAATTGCAAATAAC
TTAAGCGCTTCTACAGTTTCTTTAACCTATAATAATCAAACATTTTTCACTGATATTTTAAATACTTCATTAGAT
CCAAATGGAGTAAGAGGAAATTATGGTTCTTATACACTTGTAGAAGGTCCTATTATTGAATTTTCTCAAGGAACT
AATATCTTTAAACTAAGATCACAAAAAGGAGAATTCGCTATAGATTCCATTATTTTTAGTCCTGTTTCATAA

Figure 10

*BACILLUS THURINGIENSIS* STRAIN, CRYSTAL GENE AND CRYSTAL PROTEIN AND USES THEREOF

CROSS REFERENCE TO RELATED APPLICATIONS

This application claims priority on U.S. provisional application no. 60/448,883, filed on 24 Feb. 2003. All documents above are herein incorporated by reference.

FIELD OF THE INVENTION

The present invention relates to a novel *Bacillus thuringiensis* strain, crystal gene and crystal protein and uses thereof. More specifically, the present invention is concerned with a novel *Bacillus thuringiensis*, novel Cry31 protoxin and toxin, nucleotide sequences encoding same and anti-cancer therapeutic applications for the toxin.

BACKGROUND OF THE INVENTION

*Bacillus thuringiensis* has been known for years for coding for δ-endotoxin crystal proteins. A large variety of endotoxins have been described and characterized, many of them having reported insecticidal activities. Most of these have molecular weights in the range of 130-140 kDa and 65-80 kDa (Schnepf et al., 1998). Recently, a novel endotoxin protein has been identified and designated Cry31Aa1 (also called parasporin) (Mizuki et al., 2000). It is an 81 KDa protein encoded by a 2169 bp gene that has been characterized as having a selective activity as a human Leukemic Cell-Recognizing Protein (Mizuki et al., (1999) and (2000)). No other member of this novel family of endotoxin has yet been reported.

It is therefore an object of the present invention to provide a new *bacillus thuringiensis* strain expressing a new member of this novel family of δ-endoxins displaying advantageous cytotoxicity against human cancer cells.

SUMMARY OF THE INVENTION

More specifically, in accordance with the present invention, there is provided a novel *Bacillus thuringiensis* strain, named M15, a novel 83-kDa crystal protein δ-endotoxin assigned the designation Cry31Aa2 by the *Bacillus thuringiensis* Pesticide Crystal Protein Nomenclature Committee and displaying cytotoxicity against certain human cancer cells.

According to a first aspect of the present invention, there is also provided a biologically pure culture of a microorganism strain comprising all of the identifying characteristics of a *Bacillus thuringiensis* strain deposited at the International Depository Authority of Health Canada in Winnipeg under accession number IDAC010201-5, or a mutant thereof derived from said strain.

According to a second aspect of the present invention, there is also provided An isolated nucleic acid molecule comprising a polynucleotide sequence selected from the group consisting of: (a) a nucleotide sequence encoding a polypeptide comprising the complete amino acid sequence in SEQ ID NO: 2; (b) a nucleotide sequence encoding a polypeptide comprising the complete amino acid sequence in SEQ ID NO: 8; (c) a nucleotide sequence encoding a polypeptide comprising the complete amino acid sequence in SEQ ID NO: 12, with the proviso that said nucleotide sequence does not encode the amino acid sequence in SEQ ID NO: 18; (d) a nucleotide sequence encoding a polypeptide comprising the complete amino acid sequence in SEQ ID NO: 13, with the proviso that said nucleotide sequence does not encode the amino acid sequence at positions 232 to 723 of SEQ ID NO: 18; (e) a nucleotide sequence encoding a polypeptide comprising the complete amino acid sequence in SEQ ID NO: 14, with the proviso that said nucleotide sequence does not encode the amino acid sequence in SEQ ID NO: 18; (f) a nucleotide sequence encoding a polypeptide comprising the complete amino acid sequence in SEQ ID NO: 15, with the proviso that said nucleotide sequence does not encode the amino acid sequence at positions 232 to 723 of SEQ ID NO: 18; (g) a nucleotide sequence encoding a polypeptide comprising the complete amino acid sequence of a crystal protein contained in the *Bacillus thuringiensis* strain deposited at the International Depository Authority of Health Canada in Winnipeg under accession number IDAC010201-5; (h) a nucleotide sequence encoding a crystal protein comprising the complete amino acid sequence in SEQ ID NO: 10; (i) a nucleotide sequence comprising the sequence set forth in SEQ ID NO: 1; (j)

a nucleotide sequence comprising the sequence set forth in SEQ ID NO: 9; (k) a nucleotide sequence encoding a crystal protein comprising the sequence set forth in SEQ ID NO: 11; (l) a nucleotide sequence encoding a crystal protein having at least 94% identity with the complete amino acid sequence in SEQ ID NO: 2, with the proviso that said nucleotide sequence does not encode the amino acid sequence in SEQ ID NO: 18; (m) a nucleotide sequence encoding a crystal protein having at least 97% identity with the complete amino acid sequence in SEQ ID NO: 8 with the proviso that said nucleotide sequence does not encode the amino acid sequence from position 232 to 723 of SEQ ID NO: 18; (n) a nucleotide sequence encoding a crystal protein cytotoxic against at least one human cancer cell, said nucleotide sequence having at least 98% identity with the complete sequence set forth in SEQ ID NO: 9, with the proviso that said nucleotide sequence does not encode the amino acid sequence from position 232 to 723 of SEQ ID NO: 18; (o) a nucleotide sequence completely complementary to any of the nucleotide sequences in (a), (b), (c), (d), (e), (f), (g), (h), (i) (j), (k), (l), (m) and (n); and (p) a nucleotide sequence which hybridizes under high stringency conditions to any of the nucleotide sequences in (a), (b), (c), (d), (e), (f), (g), (h), (i) (j), (k), (l), (m), (n) and (o).

An isolated polypeptide comprising a sequence selected from the group consisting of: (a) an amino acid as set forth in SEQ ID NO: 2; (b) an amino acid sequence in SEQ ID NO: 8; (c) an amino acid sequence of a crystal protein contained in the *bacillus thuringiensis* strain in the deposit at the International Depository Authority of Health Canada in Winnipeg under accession number IDAC010201-5; (d) a crystal protein comprising the amino acid sequence in SEQ ID NO: 10; (e) a crystal protein having at least 94% identity with the complete amino acid sequence in SEQ ID NO: 2, with the proviso that said crystal protein is not constituted of SEQ ID NO: 18; (f) a crystal protein having at least 97% identity with the complete amino acid sequence in SEQ ID NO: 8, with the proviso that said crystal protein is not constituted the amino acid sequence at positions 232 to 723 of SEQ ID NO: 18; (g) a crystal protein cytotoxic against at least one human cancer cell and encoded by a nucleotide sequence having at least 98% identity with the complete sequence in SEQ ID NO: 9, with the proviso that said nucleotide sequence does encode the amino acid sequence at positions 232 to 723 of SEQ ID NO: 18.

According to an other aspect of the present invention, there is also provided a recombinant vector comprising an isolated nucleotide sequence of the present invention, a recombinant host cell same, a method for making same comprising inserting such isolated nucleic acid molecule in a vector.

According to an other aspect of the present invention, there is also provided a recombinant method for producing a cytotoxic polypeptide, comprising culturing the host cell under conditions such that the polypeptide is expressed and recovering said polypeptide.

According to an other aspect of the present invention, there is also provided an isolated antibody that binds specifically to a polypeptide of the present invention.

According to an other aspect of the present invention, there is also provided a method of modulating the level of cry31Aa2 active protein in a cell comprising a modulation of the level or activity of the sequence SEQ ID NO: 8.

According to an other aspect of the present invention, there is also provided a method of using a polypeptide of the present invention for lysing a human cancer cell which according a specific embodiment of the present invention is selected from the group consisting of HELA, TCS, HL-60, Jurkat, and Hep-G2 cells.

According to an other aspect of the present invention, there is also provided a method of testing the cytotoxicity of a polypeptide of the present invention against a candidate cancer cell comprising determining the EC50 of the polypeptide on the candidate cell, wherein the polypeptide is characterized as possessing cytotoxicity against the candidate cell if the EC50 of the polypeptide against the candidate cell is measurably lower than that against a normal T cell.

According to an other aspect of the present invention, there is also provided a method for lysing a human cancer cell comprising applying a cytotoxic amount of a polypeptide of the present invention on a human cancer cell.

According to an other aspect of the present invention, there is also provided a method for obtaining a cytotoxic polypeptide comprising cleaving a polypeptide of the present invention with a protease able to cleave between a residue R and a residue I. In a specific embodiment, the protease is trypsin.

In order to provide a clear and consistent understanding of terms used in the present description, a number of definitions are provided hereinbelow.

Unless defined otherwise, the scientific and technological terms and nomenclature used herein have the same meaning as commonly understood by a person of ordinary skill to which this invention pertains. Generally, the procedures for molecular biology methods and the like are common methods used in the art. Such standard techniques can be found in reference manuals such as for example Sambrook et al. (1989, Molecular Cloning—A Laboratory Manual, Cold Spring Harbor Laboratory Press, Cold Spring Harbor, N.Y.) and Ausubel et al. (1994, Current Protocols in Molecular Biology, Wiley, New York).

The terminology "human cancer cell" as used herein refers to cells associated with at least one type of cancer. Without limiting the generality of this definition, this terminology includes the following cells and corresponding tissues, namely acetabulum: HT-1080; amnion: WISH; B-cells: NAGL-1; blood: J-111, IM-9, jurkat; bone: HOS, MG-63, MEG-01; bone marrow: A549; MEG-01; FS-1; brain: SF126, U-251, MG, Becker, Marcus, T98G, SK-MG-1, ONS-76, KNS, B2-17, no. 10, no. 11, KALS-1, KINGS-1, KS-1, KNS-81-FD, NMC-G1, GB-1, AM-38, YH-13; colon: WiDr, LoVo, CCD 841, CCD-33, Caco-2; embryonic limb: Miz-1; epidermoid: A-431; whole fetus: HE-1; foreskin: FLOW7000, Hs68, liver: Chang Liver, Alexander cells, HC, Hep-G2; lung: MRC-5, MRC-9, HFL1, WI-38, Flow 2000, KNS-62; lymph node: GAK; lymphoblastoid: Namalwa; maxilla: Raji; melanoma: G-361, A2058; neuroblastoma: KP-N; ovary: RMG, RKN, RTSG, RMUG; peripheral blast: MTA; peripheral blood: RPMI 8226, HL-60, CCRF-SB, EB-3, RPMI 788, NC-37, MOLT-4, KU812, CCRF-CEM, CMK, NOMO, NKM-1, MEG-A2, TMD5, KAI3; pleural effusion: U-937; prostate: DU145, CEACAM-1; sympatho-adrenal cell: IMR-32, NB-1; umbilical cord: HUV-EC-C; uterine cervix: Ca Ski, HeLa, SKG, BOKU; uterine endometrium: SNG; uterus: SKN, NJG, SAWANO, TCS, UtSMC. The terminology "cancer cell" also refers herein to cells associated with non-human forms of cancer including Vero, COS-7 and NIH3T3 cells.

As used herein, a "biologically pure" strain is intended to mean the strain separated from materials with which it is normally associated in nature. Note that a strain associated with other strains, or with compounds or materials that it is not normally found with in nature, is still defined as "biologically pure." A monoculture of a particular strain is, of course, "biologically pure."

Nucleotides

Nucleotide sequences of the present invention are presented herein by single strand, in the 5' to 3' direction, from left to right, using the one letter nucleotide symbols as commonly used in the art and in accordance with the recommendations of the IUPAC-IUB Biochemical Nomenclature Commission.

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (e.g. genomic DNA, cDNA), RNA molecules (e.g. mRNA) and chimeras thereof. The nucleic acid molecule can be obtained by cloning techniques or synthesized. DNA can be double-stranded or single-stranded (coding strand or non-coding strand [antisense]).

Protein Expression

Prokaryotic expressions are useful for the preparation of large quantities of the Cry31Aa2 protoxine and toxine encoded by the cry31Aa2 DNA sequence. These proteins can be purified according to standard protocols that take advantage of the intrinsic properties thereof, such as size and charge (e.g. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications in accordance with the methods and uses of the present invention.

Mutations, Mutants and Variants

As commonly known, a "mutation" is a detectable change in the genetic material which can be transmitted to a daughter cell. As well known, a mutation can be, for example, a detectable change in one or more deoxyribonucleotides. For example, nucleotides can be added, deleted, substituted for, inverted, or transposed to a new position. Spontaneous mutations and experimentally induced mutations exist. A mutant polypeptide can be encoded from this mutant nucleic acid molecule.

As used herein, a "mutant" of the novel strain of *Bacillus thuringiensis* of the present invention namely the M15 strain deposited under access no, IDAC010201-5 may or may not have the same identifying biological characteristics of the M15 strain, as long as the mutant produces a crystal protein that is cytotoxic against human cancer cells. Illustrative examples of suitable methods for preparing mutants and variants of the inventive microorganism strain include, but are not limited to: mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by insertional elements or transposons or by homologous recombination of transforming linear or circular DNA molecules; and transduction mediated by bacteriophages such as P1. These methods are well known in the art and are described, for example, in J. H. Miller, Experiments in Molecular Genetics, Cold Spring Harbor Laboratory Press, Cold Spring Harbor, N.Y. (1972); J. H. Miller, A Short Course in Bacterial Genetics, Cold Spring Harbor Laboratory Press, Cold Spring Harbor, N.Y. (1992); M. Singer and P. Berg, Genes & Genomes, University Science Books, Mill Valley, Calif. (1991); J. Sambrook, E. F. Fritsch and T. Maniatis, Molecular Cloning: A Laboratory Manual, 2d ed., Cold Spring Harbor Laboratory Press, Cold Spring Harbor, N.Y. (1989); P. B. Kaufman et al., Handbook of Molecular and Cellular Methods in Biology and Medicine, CRC Press, Boca Raton, Fla. (1995); Methods in Plant Molecular Biology and Biotechnology, B. R. Glick and J. E. Thompson, eds., CRC Press, Boca Raton, Fla. (1993); and P. F. Smith-Keary, Molecular Genetics of *Escherichia coli*, The Guilford Press, New York, N.Y. (1989).

Mutated strains derived from the M15 strain using known methods are then preferably selected or screened for improved cytotoxic crystal proteins production potential or for other desirable properties related to their utility in expressing crystal proteins that are cytotoxic to human cancer cells. In a specific embodiment of the mutagenesis and screening approach to strain improvement, mutagenized cells are selected on the basis of their cytopathic effects or cytocidal activity on target cells and their spectrum of action.

The term “variant” refers herein to a protein or nucleic acid molecule which is substantially similar in structure and biological activity to the protein or nucleic acid of the present invention and includes a cry31Aa2 nucleic sequence or the protein encoded by same having one or more mutations that does not affect its cytotoxic activity. In particular, a variant of the nucleotide or polypeptide sequence of the active portion of Cry31Aa2 possesses the ability to lyse human cancer cells including HeLa, TCS, HL-60, Jurkat and Hep-G2. The methods for determining whether a nucleotide or polypeptide sequence constitutes a variant of Cry31Aa2 include conducting an EC50 assay on a cancer cell against which the Cry31Aa2 active toxin displays cytotoxicity.

The functional derivatives of the present invention can be synthesized chemically or produced through recombinant DNA technology. All these methods are well known in the art.

Hybridization

“Nucleic acid hybridization” refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra, and Ausubel et al., 1989, supra) and are commonly known in the art. In the case of an hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5× Denhardt’s solution, 1% SDS, and 100 μg/ml denatured carrier DNA (e.g. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al.,1989, supra). In most hybridizations, a 1% mismatching of bases will lower the melting temperature by 1-1.5° C. (Sambrook et al.,1989, supra). Consequently, nucleotide sequences sharing 98% nucleotide identities with the cry31Aa2 gene encoding the trypsin-activated portion of Cry31Aa2 will still hybridize with the cry31Aa2 gene when the melting temperature is lowered by 3° C., respective to the most stringent conditions for hybridization between two identical cry31Aa2 sequences. The term “high stringency” conditions refer herein to the conditions required for the hybridization of nucleotide sequences sharing at least 98% nucleotide identities with the cry31Aa2 gene encoding the trypsin-activated portion of Cry31Aa2.

As used herein, “chemical derivatives” is meant to cover additional chemical moieties not normally part of the subject matter of the invention. Such moieties could affect the physico-chemical characteristic of the derivative (e.g. solubility, absorption, half life, decrease of toxicity and the like). Such moieties are exemplified in Remington’s Pharmaceutical Sciences (1980). Methods of coupling these chemical-physical moieties to a polypeptide or nucleic acid sequence are well known in the art.

Recombinant Vectors

The term “recombinant DNA” as known in the art refers to a DNA molecule resulting from the joining of DNA segments. This is often referred to as genetic engineering. The same is true for “recombinant nucleic acid”.

The term “vector” is commonly known in the art and defines a plasmid DNA, phage DNA, viral DNA and the like, which can serve as a DNA vehicle into which DNA of the present invention can be cloned. Numerous types of vectors exist and are well known in the art.

The term “expression” defines the process by which a gene is transcribed into mRNA (transcription), the mRNA is then being translated (translation) into one polypeptide (or protein) or more.

The terminology “expression vector” defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a “reporter sequence” are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain −10 and −35 consensus sequences, which serve to initiate transcription and the transcript products contain Shine-Dalgarno sequences, which serve as ribosome binding sequences during translation initiation.

Recombinant Host Cell

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra).

Method for Identifying Other Cancer Cells Against Which Cry31Aa2 is Cytotoxic

In addition to the EC50 assay described herein, other assays may be used to determine the effects of Cry31Aa2 or other proteins encompassed by the present invention on human cancer cells. In particular, these effects may be observed by photonic microscopy. Furthermore, assays for detecting cytopathic effects can also be used for this purpose.

Other objects, advantages and features of the present invention will become more apparent upon reading of the following non-restrictive description of preferred embodiments thereof, given by way of example only with reference to the accompanying drawings.

The present invention seeks to meet these needs and other needs.

The present description refers to a number of documents, the content of which is herein incorporated by reference in their entirety.

BRIEF DESCRIPTION OF THE DRAWINGS

In the appended drawings:

FIG. 3 is the nucleotide sequence of the translated portion of the cry31Aa2 gene (SEQ ID NO: 1);

FIG. 4 is the deduced amino acid sequence of the cry31Aa2 gene (SEQ ID NO: 2);

FIG. 5 shows a comparison of the deduced amino acid sequences of Cry31Aa2 (SEQ ID NO: 2) and Cry31Aa1 (SEQ ID NO: 18). The capital letters and dotted lines under the amino acid sequence of Cry31Aa2 (SEQ ID NO: 2) correspond to the difference and alignment gaps between the cry31Aa2 (SEQ ID NO: 2) and Cry31Aa1 (SEQ ID NO: 18). The asterisks under the Cry31Aa2 sequence indicate the identities between Cry31Aa2 (SEQ ID NO: 2) and Cry31Aa1(SEQ ID NO: 18);

FIG. 9 shows the nucleotide sequence (SEQ ID NO: 16) and deduced amino acid sequence (SEQ ID NO: 2) of the cry31Aa2 gene along with features thereof; and FIG. 10 shows the nucleotide sequence of the translated portion of the cry31Aa1 gene (SEQ ID NO: 17).

DESCRIPTION OF THE PREFERRED EMBODIMENT

Figure 1A:
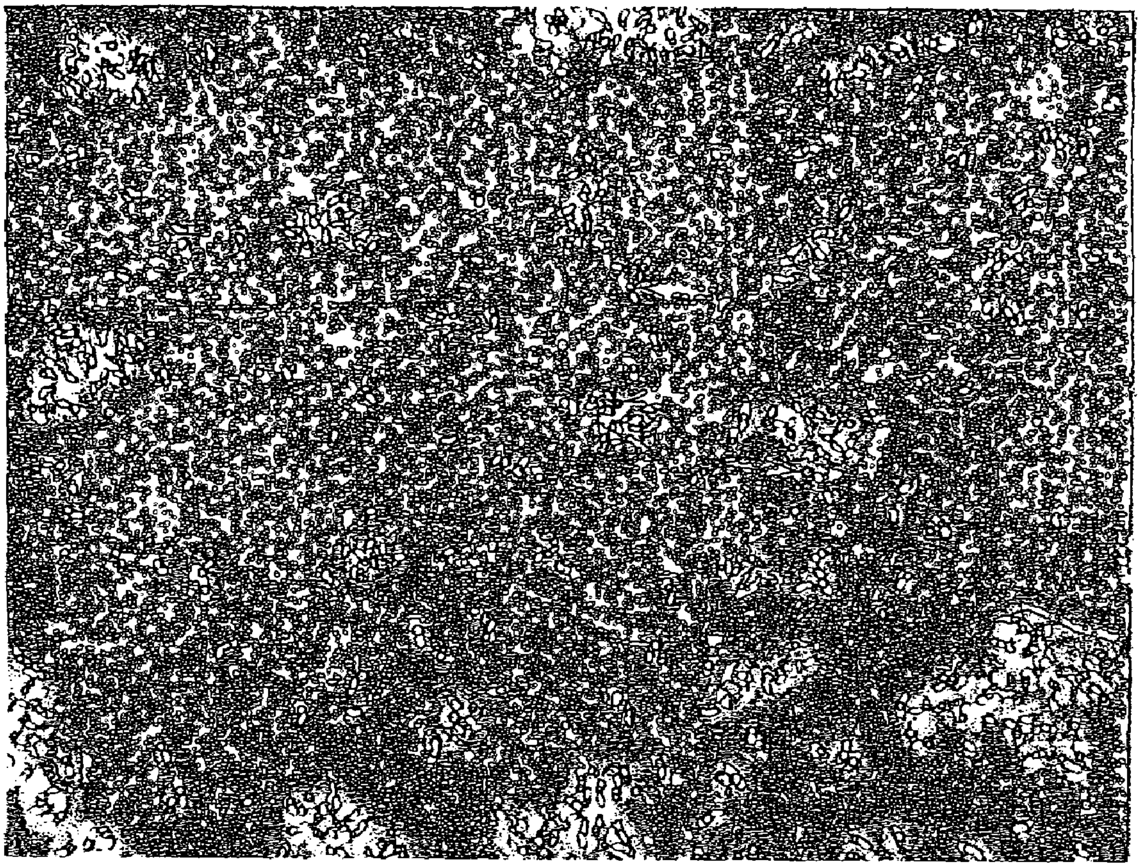
FIG. 1 illustrates in panel A) a phase-contrast micrograph of a lysed culture of *Bacillus thuringiensis* strain M15; in panel B, a transmission electron micrograph of *Bacillus thuringiensis* strain M15 containing a spore and a tightly bound parasporal inclusion.

Isolation of Strain, Morphological and Biochemical Characteristics

A *Bacillus thuringiensis* strain was isolated from dead two-spotted spider mites (*Tetranychus urticae* Koch; Arthropoda: Arachnida: Tetranychidae) and named M15. The mites, parasitic on apple leaves, were collected in an apple orchard located in Frelighsburgh, Quebec, Canada. They were homogenized in 3 ml of phosphate-buffered saline (PBS) (NaCl 8 g, KCl 0.2 g, Na2HPO4 1.44 g, KH2PO4 0.24 g I-1). The homogenized solution was incubated for 16 hr at room temp and heated at 78° C. for 15 min. Afterwards, the homogenate was plated on 2YT agar medium (Bacto Tryptone 16 g, Bacto Yeast Extract 10 g, NaCl 5 g, Agar 18 g I-1), and incubated for 24 hr at 30° C. All colonies with a morphology similar to *B. thuringiensis* were streaked on T3 agar medium (Bacto Tryptone 3 g, Bacto Tryptose 2 g, Bacto Yeast Extract 1.5 g, MnCl2 0.005 g, 0.05M Sodium phosphate, pH6.7, Agar 18 g I-1) and incubated at 30° C. for 48 hr. The cultures were examined by phase-contrast microscopy (Carl Zeiss Canada Ltd., Toronto, Ontario, Canada) for the presence of spores and crystals. *B. thuringiensis* M15 was deposited on 29 January 2001 in the International Depository Authority of Health Canada in Winnipeg under the Budapest Treaty (Bureau of Microbiology, Health Canada, 1015 Arlington Street, Winnipeg, Manitoba, R3E 3R2) under accession no. IDAC010201-5.

The M15 strain was characterized for its ability to ferment specific carbon sources, and for the production, utilization and reduction of specific compounds (see Table 1 below). The biochemical characteristics of *B. thuringiensis* strain M15, obtained using the API 50CH and API 20E kits as recommended by the manufacturer (bioMérieux, St-Laurent, Quebec, Canada), were different from those of three controls, *B. thuringiensis* var. *kurstaki* HD-1, -var. *israelensis* HD-500 and -var. *higo* BT205. *B. thuringiensis* var. *kurstaki* HD-1 and -var. *israelensis* HD-500 were obtained from "Laboratoire des bactéries entomopathogénes", Institut Pasteur (Paris, France). *B. thuringiensis* var. *higo* BT205 was in the Agriculture Canada collection (Jung et al., 1998). The M15 strain is further characterized in Jung, 2001.

TABLE 1

| | The biochemical profile of *B. thuringiensis* M15 and selected control strains | | | |
|---|---|---|---|---|
| Tests | *B. thuringiensis* var. *kurstaki* HD-1 | *B. thuringiensis* var. *israelensis* HD-500 | *B. thuringiensis* var. *higo* BT 205 | *B. thuringiensis* M15 |
| Fermentation of | | | | |
| Glycerol | + | + | + | ± |
| D-Arabinose | − | − | − | − |
| L-Arabinose | − | − | − | − |
| Ribose | + | + | + | + |
| D-Xylose | − | − | − | − |
| L-Xylose | − | − | − | − |
| D-Galactose | − | − | − | − |
| D-Glucose | + | + | + | + |
| D-Fructose | + | + | + | + |
| D-Mannose | − | − | − | − |
| L-Sorbose | − | − | − | − |
| Inositol | − | − | − | − |
| D-Mannitol | − | − | − | − |
| D-Sorbitol | − | − | − | − |
| N-Acetylglucosamine | + | + | + | + |
| Arbutin | + | + | + | − |
| Esculin | + | ± | + | ± |
| Salicin | + | − | + | + |
| D-Cellobiose | + | + | + | − |
| D-Maltose | + | + | + | + |
| Lactose | − | − | − | − |
| Melibiose | − | − | − | − |
| Sucrose | − | − | − | − |
| Trehalose | + | + | + | + |
| Starch | − | + | + | − |
| Glycogen | + | + | + | − |
| Gluconate | + | + | ± | − |
| Production of | | | | |
| β-Galactosidase | − | − | − | − |
| Arginine dihydrolase | + | + | + | − |
| Ornithine decarboxylase | − | − | − | − |
| Urease | + | − | + | + |
| Tryptophane deaminase | − | − | − | − |
| Gelatinase | + | + | + | + |
| Oxidase | + | + | + | + |
| Catalase | + | + | + | + |
| $H_2S$ | − | − | − | − |
| Indole | − | − | − | − |
| Acetoin | + | + | + | + |
| Citrate utilization | + | − | − | − |
| Nitrate reduction | + | − | − | − |

+, −, and ± indicate positive, negative, and weak reactions, respectively.

Microscopic Characterization of Cry31Aa2 Parasporal Inclusion Bodies

Figure 1B:
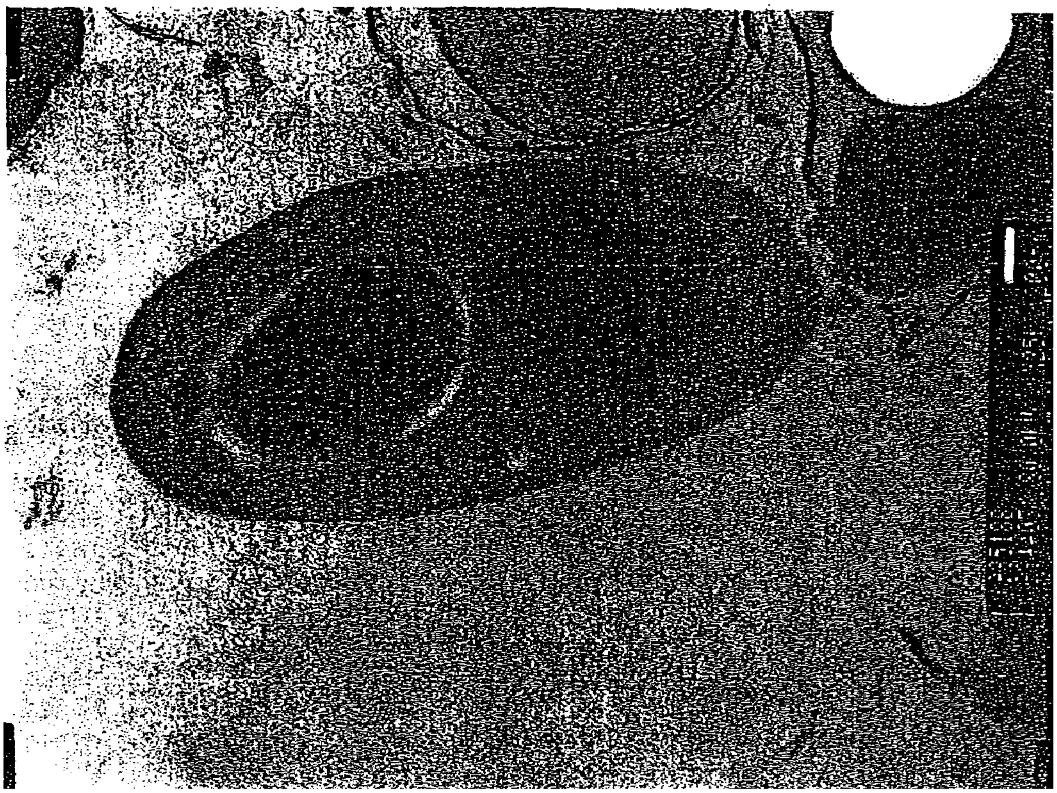

The parasporal inclusion bodies produced by a sporulated culture of *B. thuringiensis* strain M15 appear roughly spherical when observed under phase-contrast microscopy (FIG. 1A) and are tightly coupled to the spores even in lysed cultures. Further analysis under the transmission electron microscope (TEM), however, reveals that the parasporal inclusion body has a polygonal shape (FIG. 1B). The TEM observation was conducted after the *B. thuringiensis* strain M15 was incubated for 5 days at 30° C. in T3 medium and the samples ultra-thinly sectioned according to Beveridge et al. (1994). Arrows show the roughly spherical parasporal inclusions tightly bound to the white ovoid spores. In this figure, "S" and "P" denote spore and parasporal inclusion, respectively. Magnification used is of 25,000×.

SDS-PAGE Analysis and N-terminal Sequencing of the Native Parasporal Inclusion Protein The *B. thuringiensis* strain M15 was grown in T3 medium for 5 days at 30° C. on a rotary shaker to allow crystal protein production. Spores and crystals were separated from each other in the tightly bound parasporal duplexes using an ultrasonic processor model VC130 (Sonics & Materials, Inc., Newtown, Conn., USA) and purified by sucrose density gradient centrifugation as described elsewhere (Thomas and Ellar, 1983). Twenty microliters of the crystal suspension were added to 3 volumes of gel loading buffer (4% SDS, 20% glycerol, 125 mM Tris-HCl, 10% 2-mercaptoethanol, pH 6.8) in a 1.5-ml microtube, incubated at 90° C. for 7 min and centrifuged for 2 min to remove unsolubilized materials. Thirty microliters of the supernatant were loaded on top of 10% SDS-polyacrylamide gels. Discontinuous sodium dodecyl sulfate-polyacrylamide gel electrophoresis (SDS-PAGE) was performed according to Laemmli and Favre (1973).

Figure 2:
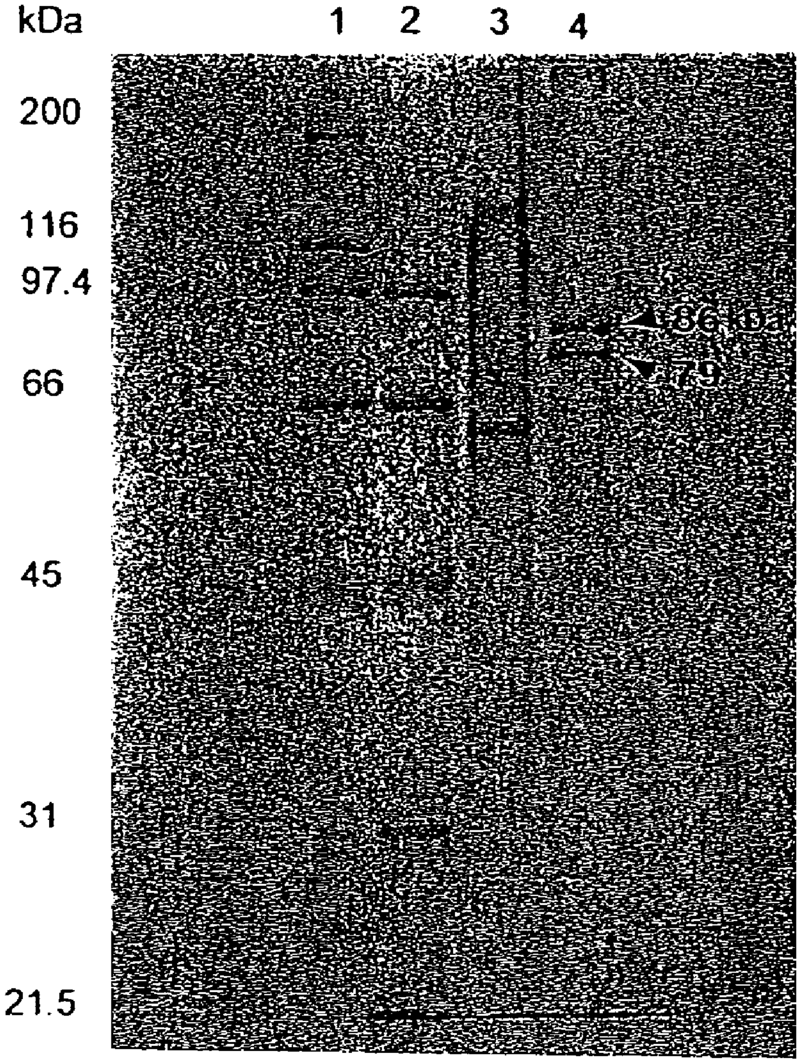
FIG. 2 shows a SDS-PAGE analysis of the parasporal inclusion protein(s) of *B. thuringiensis* strain M15.

FIG. 2 shows the *B. thuringiensis* strain M15 parasporal inclusion purified by sucrose density gradient centrifugation as subjected to a 10% SDS-PAGE electrophoresis (lane 4); the crude extracts of the fully lysed *B. thuringiensis* var. *kurstaki* HD-1 subjected to electrophoresis on the same gel (lane 3) as a control; and high molecular (lane 1) and low molecular masses (lane 2) of standard protein markers on the left. At least two major bands of approximately 86- and 79-KDa in size were revealed. They were transferred to a polyvinylidene difluoride (PVDF) membrane (Bio-Rad™), excised and subjected to a pulsed liquid phase sequencer for determination of N-terminal amino acid sequence.

The N-terminal amino acid sequence of the crystal protein from *B. thuringiensis* strain M15 was determined as follows. The purified parasporal crystal was added into 0.1N NaOH-3M HEPES solution and solubilized in 10 volumes of gel loading buffer by incubating in boiling water for 5 min. The crystal protein was separated on 10% SDS-PAGE and transferred to a polyvinylidene difluoride (PVDF) membrane (Bio-Rad, Mississauga, Ontario, Canada). The crystal protein band stained with Coomassie brilliant blue™ R-250 (Bio-Rad) was excised and subjected to a pulsed liquid phase sequencer model 473A (Applied Biosystems, Foster City, Calif., USA) at the Regional Sequencing Facility (Centre de recherche du Centre hospitalier de l'Université Laval, Quebec, Canada).

The N-terminal sequence analysis revealed that both polypeptides (86- and 79-KDa) shared identical 20-amino acids residues. These were Met, Asp, Pro, Phe, Ser, Asn, Tyr, Ser, Glu, Gln, Lys, Tyr, Pro, Asp, Ser, Asn, Asn, Asn, Gln and Glu (SEQ ID NO: 3).

Southern Hybridization and Gene Cloning

An 18-mer oligonucleotide sequence, referred to as M15-M, was deduced from a middle portion of the N-terminal amino acid sequence (Glu, Gln, Lys, Tyr, Pro, Asp (SEQ ID NO: 4)) of the 86-kDa crystal protein. The M15-M oligonucleotide was labeled by the Digoxigenin (DIG) oligonucleotide 3'-end labeling kit containing DIG-11-ddUTP (Roche, Laval, Quebec, Canada) as recommended by the manufacturer. The labeled oligonucleotide was precipitated with 0.1 volume of 4M LiCl and 2.5 volumes of ice-cold ethanol, and transferred at −70° C. for 30 min. The reaction was centrifuged at 16,000 g for 15 min at 4° C. The washed pellet was resuspended in nuclease-free water, and stored at −20° C. until use.

The M15-M generated had the following sequence: 5'-GARCARAARTAYCCNGAY-3' (SEQ ID NO: 5).

*B. thuringiensis* strain M15 was grown in Luria-Bertani (LB) medium (Bacto Tryptone 10 g, Bacto Yeast Extract 5 g, NaCl 5 g I-1) at 30° C. for 16 hr on a rotary shaker. Plasmid DNA was isolated using the alkaline extraction method as described elsewhere (Birnboim and Doly, 1979) with the following modifications. Lysozyme™ (Sigma-Aldrich Canada Ltd., Oakville, Ontario, Canada) was added at a concentration of 2 mg.ml-1 and the cell suspension was incubated at 37° C. for 1 hr.

The plasmid DNA was then purified with Wizard™ Plus SV minipreps DNA purification system following the manufacturer's recommendation (Promega, Nepean, Ontario, Canada). Three samples of the plasmid were then digested with HindIII, HindIII/EcoRI and EcoRI (Gibco BRL), respectively, electrophoresed on a 0.7% agarose gel and transferred onto a Nytran™ nylon membrane (Schleicher & Schuell, Keene, N.H., USA) by the method of Southern (1975). They were then probed with the DIG-labeled 18-mer M15-M oligonucleotide.

This Southern blot hybridization was performed using the DIG-labeled oligonucleotides with the standard hybridization solution (5×SSC, 1% blocking reagent (Roche), 0.1% N-lauroylsarcosine, 0.02% SDS) for 13 hr at 39° C. After hybridization, the membrane was washed twice for 15 min each in 4× wash solution (4×SSC, 0.1% SDS) at 39° C. Following the washes, detection of signals on the membrane was performed with the color-substrate solution containing NBT (4-Nitroblue tetrazolium chloride, Roche) and BCIP (5-Bromo-4-chloro-3-indolyl-phosphate, Roche) as recommended by the manufacturer. After hybridization and post-hybridization washes at 39° C., the M15-M probe strongly hybridized to an 8-kb HindIII, a 2.6-kb HindIII/EcoRI, and a 2.6-kb EcoRI fragment.

The purified *B. thuringiensis* M15 plasmid DNA was digested with HindIII and ligated with the HindIII-digested SAP (Shrimp Alkaline Phosphatase, Roche)-treated pBluescript™ II KS(+) (Stratagene, La Jolla, Calif., USA). After ligation, the recombinant DNA was transformed into *E. coli* DH5α (Gibco BRL, Burlington, Ontario, Canada). Preparation of *E. coli* DH5α competent cells and transformation were done as described (Sambrook et al., 1989).

The transformants were grown on LB agar plates containing 100 μg ml-1 ampicillin (Sigma-Aldrich Canada Ltd.) and 40 μg ml-1 X-Gal (5'-Bromo4-chloro-3-indolyl-β-D-galactopyranoside, Sigma-Aldrich Canada Ltd.) at 37° C. White colonies were toothpicks-transferred to 1 ml of fresh LB media supplemented with 100 μg ml-1 ampicillin, and incubated overnight at 37° C.

The recombinant DNA were then isolated by the cracking procedure (Sambrook et al., 1989) and electrophoresed on 0.7% agarose gel to assess the size of the undigested recombinant plasmids.

The three recombinant plasmids with the highest molecular weight were selected and digested with HindIII. They were designated pYCH27, pYCH40 and pYCH217, respectively. All three plasmids contained an 8-kb HindIII insert. In addition, pYCH27 and pYCH40 also contained a 0.75-kb and a 1.9-kb HindIII fragment, respectively. They were then electrophoresed on a 0.7% agarose gel, transferred onto a Nytran™ nylon membrane by the method of Southern (1975) and probed with the M15-M oligonucleotide. The M15-M probe hybridized to the 8-kb HindIII fragments in pYCH27, pYCH40 and pYCH217 as revealed by Southern blot hybridization.

The 8-kb HindIII fragments from pYCH27, pYCH40 and pYCH217 were doubly digested with HindIII/EcoRI, electrophoresed on agarose gel, Southern transferred, and hybridized with the M15-M probe. For each of the three recombinant plasmids, a single 2.6-kb fragment was detected (data not shown). This confirms that this 2.6-kb fragment is the same as the one in the EcoRI-digested plasmid DNA of strain M15.

The 8-kb HindIII insert was excised from recombinant plasmid pYCH217, digested with various restriction enzymes [EcoRI, *Bg/II* (Gibco BRL), DraI, SphI (Amersham Pharmacia Biotech)], and a restriction map constructed. The 8-kb HindIII fragment contains a 3.4-kb HindIII/EcoRI, a 2.6-kb EcoRI/EcoRI, a 1.4-kb EcoRI/EcoRI and a 0.6-kb EcoRI/HindIII fragment.

To identify the region homologous to the M15-M probe, the recombinant plasmid pYCH217 was doubly digested with HindIII/EcoRI, and the resulting fragments were subcloned into EcoRI-digested pBluescript™ II KS(+). After ligation, four subclones were obtained to give the recombinant plasmids pYC12S, pYC22S, pYC30S, and pYC31S. Plasmids pYC12S and pYC30S contained a 1.4-kb and a 2.6-kb insert, respectively, while pYC22S and pYC31S both harbored a 2.6-kb insert along with a 0.6-kb and a 1.4-kb fragment, respectively. Only the 2.6-kb EcoRI/EcoRI fragment from subclones, pYC22S, pYC30S and pYC31S hybridized with the M15-M probe. To further localize the region of hybridization of the M15-M probe in the 2.6-kb EcoRI/EcoRI fragment, the recombinant plasmid pYC30S was digested with EcoRI, EcoRI/DraI, EcoRI/SphI, and EcoRI/BglII, respectively, and then hybridized with the M15-M probe. The M15-M probe detected a 2.6-kb EcoRI, a 0.6-kb DraI, a 1.6-kb EcoRI/SphI, and a 0.85-kb EcoRI/BglII fragment, respectively. It was thus determined that the region of hybridization of the M15-M probe lied between the BglII and DraI sites within the 2.6-kb EcoRI fragment.

Characterization of a New Crystal Protein Gene, cry31Aa2

The nucleotide sequences of the 2.6-kb EcoRI/EcoRI, 1.4-kb EcoRI/EcoRI and 0.6-kb EcoRI/HindIII fragments were determined. An open reading frame (ORF) of 2,226-bp in length that codes for a polypeptide of 742 amino acids with a predicted molecular mass of 83,068 Da (FIGS. 3 and 4) was found. The start codon is not ATG but GTG. One potential promoter-like sequence in the 5' non-coding region (Lereclus et al., 1989; Baum and Malvar, 1995) shows a 13-bp spacing between the putative −10 and −35 sequences located 138-bp upstream from the start codon (GTG). The potential ribosome binding site (RBS) (GAAAGGTGG (SEQ ID NO: 6)) is located 7-bp upstream of the start codon (GTG) and is partially complementary to the 3' end (UCUUUCCUCC (SEQ ID NO: 7)) of *B. subtilis* 16S rRNA (McLaughlin et al., 1981; Moran et al., 1982). Both potential −35 and −10 boxes and a putative ribosome-binding site are underlined in FIG. 9. The calculated free energy of interaction (ΔG, 25° C.) between the *B. subtilis* 16S rRNA and the putative ribosome binding site is −14.8 kcal-mol-1 (Tinoco et al., 1973). A terminal inverted repeat that could form a stem-and-loop secondary structure with a calculated energy (ΔG, 25° C.) of −12.2 kcal-mol-1 (Tinoco et al., 1973) is located 112-bp downstream from the stop codon (TM), which is marked with asterisks in FIG. 9, and may function as a transcription terminator (indicated by arrows). The 18-mer M15-M oligonucleotide sequence based on the N-terminal amino acid sequence (Glu, Gln, Lys, Tyr, Pro, Asp (SEQ ID NO: 4)) of the crystal protein is homologous to a region located 24-bp downstream from the start codon (GTG). The sequence of the DIG-labeled 18-mer oligonucleotide (M15-M) probe is indicated in bold capital letters in FIG. 9.

The cry31Aa2 Gene Expression in *B. thuringiensis* Cry-B Strain

Figure 6:
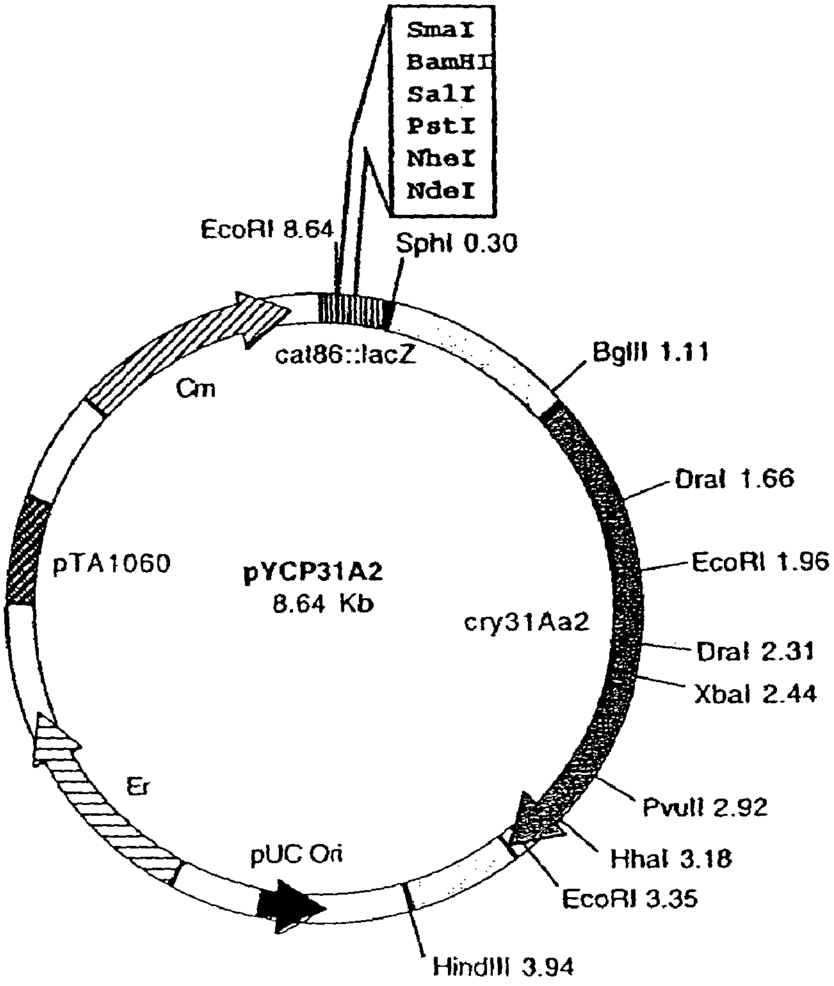
FIG. 6 shows a restriction map of the recombinant plasmid pYCP31A2 containing the cry31Aa2 gene.

The 3.6-kb HindIII/SphI fragment containing the entire crystal protein gene was excised from the recombinant plasmid pYCH217, and then cloned into the *E. coli-B. thuringiensis* shuttle vector pHPS9 doubly digested with HindIII/SphI to yield recombinant plasmid pYCP31A2 (FIG. 6). The *E. coli-B. thuringiensis* shuttle vector pHPS9 (Haima, et al., 1990) was purchased from American Type Culture Collection (Manassas, Va., USA). To express the cloned cry31Aa2 crystal protein gene in the acrystalliferous *B. thuringiensis* strain Cry-B, the 3.6-kb HindIII/SphI fragment was cloned into the HindIII/SphI doubly-digested *E. coli-B. thuringiensis* shuttle vector pHPS9 to yield recombinant plasmid pYCP31A2 (FIG. 6).

The *B. thuringiensis* var. *kurstaki* HD-1 acrystalliferous Cry-B strain ((Stahly et al., 1978) provided by the *Bacillus* Genetic Stock Center, The Ohio State University (Columbus, Ohio, USA)), was transformed with the cloned *B. thuringiensis* M15 crystal protein gene by electroporation as described by Vehmaanperä (1989) with the following modifications. Bacterial cells cultured in 200 ml of LB supplemented with 0.25 M sucrose and 0.05 M potassium phosphate, pH7.0 (LBSP) to an optical density of 1.0 at 600 nm were centrifuged, washed three times with ice-cold SHMG buffer (250 mM sucrose, 1 mM HEPES, 1 mM MgCl2, 10% (v/v) glycerol, pH 7.0), and then resuspended in 1 ml of ice-cold SHMG buffer. The cell suspension was mixed with plasmid DNA at a final DNA concentration of 10 μg ml-1 in a 0.2-cm electroporation cuvette (Bio-Rad), kept on ice for 30 min, and then electroporated by a Gene Pulser™ model 1652076 (Bio-Rad) at 25 μF, 2.5 kV and 400 Ω with the pulse once. After electroporation, 3 ml of LBSP supplemented with 10% (v/v) glycerol (LBSPG) were immediately added into the cuvette and incubated at 37° C. for 2 hr with shaking.

The selected *B. thuringiensis* transformant was cultured in 250 ml of nutrient broth supplemented with 5 μg ml-1 of erythromycin (Sigma-Aldrich Canada Ltd.) and 5 μg ml-1 of chloramphenicol (Sigma-Aldrich Canada Ltd.) at 37° C. until cell autolysis was observed. The lysate was harvested and then washed twice with 10 mM EDTA (pH 8.0)-1 M NaCl-1 mM phenylmethylsulfonyl fluoride (Sigma-Aldrich Canada Ltd.).

Figure 7:
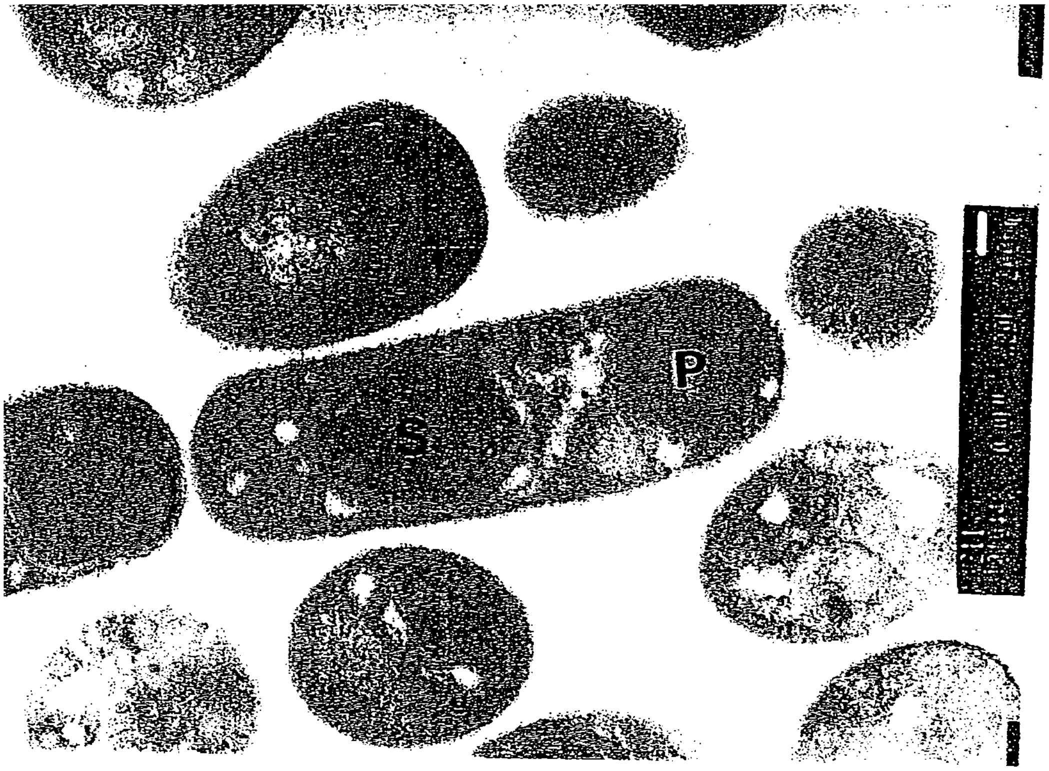
FIG. 7 shows a transmission electron micrograph of a *B. thuringiensis* Cry$^-$ B transformant expressing the cry31Aa2 gene. S: spore; P: parasporal inclusion; Magnification: 20,000×.

The *B. thuringiensis* Cry-B transformant containing the *B. thuringiensis* M15 parasporal crystal protein gene was incubated in nutrient broth (Bacto Beef Extract 3 g, Bacto Peptone 5 g I-1) at 30° C. for 3 days to allow expression of the toxin gene and crystal formation. The presence of parasporal inclusions was examined by phase-contrast microscopy. When observed under a phase-contrast microscope, the *B. thuringiensis* transformants expressing the cry31Aa2 gene contained, in addition to the spore, a roughly spherical inclusion, whereas no inclusions were found in the *B. thuringiensis* transformant harboring the non-recombinant shuttle vector pHPS9 alone (data not shown). Under the transmission electron microscope (TEM), however, the parasporal inclusion body has a nearly perfect hexagonal shape (FIG. 7). Both inclusions in the transformant, spore and crystal, are separated from each other as opposed to what is found in *B. thuringiensis* strain M15 where they are tightly bound to each other.

Figure 8:
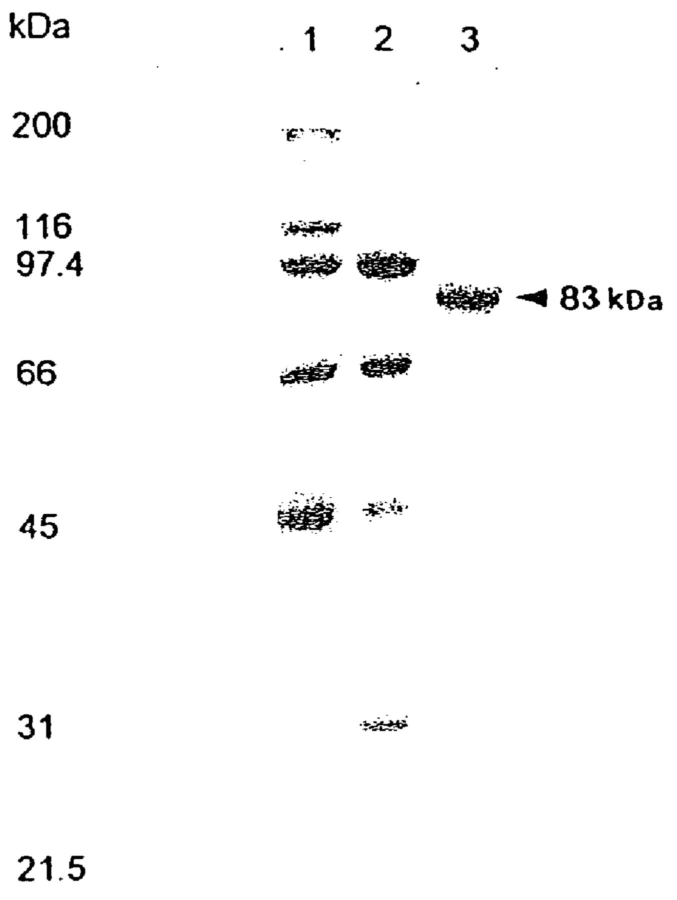
FIG. 8 shows a SDS-PAGE analysis of the parasporal inclusion protein from a *B. thuringiensis* transformant expressing the crystal protein gene cry31Aa2.

The parasporal inclusion from a *B. thuringiensis* transformant was purified by sucrose density gradient centrifugation as described previously (Thomas and Ellar, 1983). It was then subjected to a 10% discontinuous sodium dodecyl sulfate-polyacrylamide gel electrophoresis (SDS-PAGE) (lane 3) as reported previously (Laemmli and Favre, 1973). High molecular (lane 1) and low molecular masses (lane 2) of standard protein markers are indicated on the left. The parasporal inclusion protein in the *B. thuringiensis* transformant is composed of a single major polypeptide of 83-kDa (FIG. 8).

Preparation of Inclusion Proteins, Proteolvtic Processing, and Toxin Activation

The spore-inclusion mixture was harvested from sporulated cultures and the inclusions were partially purified by a biphasic separation method described in Goodman (1967) using polyethylene glycol 6000 (Wako Pure Chemical, Osaka, Japan) and sodium dextran sulfate 500 (Sigma, St. Louis, Mo.). Inclusions were further purified by sucrose density gradient centrifugation as described in Saitoh et al., (1998a). The purified inclusions were stored at 20° C. until use.

Solubilization of purified inclusions was done in 50 mM $Na_2CO_3$ (pH 10.0) containing 1 mM EDTA and 10 mM dithiothreitol for 1 h at 37° C. After centrifugation at 20,000× g for 5 min at 4° C. to remove unsolubilized materials, the pH of the solution was adjusted to 8.0.

The native 83 KDa protoxine displayed no cytocidal activity against cancer cells. This protein was therefore cleaved with three enzymes, namely trypsin, chymotrypsin and proteinase K to identify an active toxine. The solubilized proteins (1.3 mg ml) were therefore treated with proteinase K (final concentrations, 0.0003, 0.003, 0.03, and 0.3 mg ml1), trypsin (0.03, 0.3, 3, and 30 mg ml1), and chymotrypsin (0.03, 0.3, 3, and 30 mg ml1) in 50 mM Na2CO3 (pH 10.0) for 1.5 h at 37° C. After protease treatment, phenylmethylsulfonyl fluoride (Wako Pure Chemical) was added to the solution to stop the proteolytic reaction, and the mixture was examined for both sodium dodecyl sulfate-polyacrylamide gel electrophoresis (SDS-PAGE) profiles and cytopathic effect (CPE) on certain cancer cells including MOLT-4 and Hela. The CPE was monitored under a phase-contrast microscope for 24 h, and the degree of cytopathy was graded on the basis of the ratio of damaged cells as described in Mizuki et al., (1999).

One-dose Assay, Hemolytic Assay, and Dose-response Study

One-dose assays for cytotoxicity and hemolytic activity were carried out as described in Mizuki et al., (1999). Each well of a MicroTest plate received 90 μl of cell suspension containing $2\times10^4$ cells. After preincubation for 16 h at 37° C., 10 μl of the trypsin-activated sample solution (1.3 mg ml) was added to the well.

Thirteen human cells, two monkey cells and one mouse cell were used for dose-response studies. A hemolytic assay was done using human erythrocytes according to the method described in Saitoh et al., (1998b). Each well containing 90 μl of cell suspension ($2\times10^4$ cells) received 10 μl of trypsin-activated inclusion proteins which had been prepared in 10-fold serial dilutions in 50 mM $Na_2CO_3$ (pH 10.0) containing 10 mM DTT and 1 mM EDTA. Five wells were used for each dilution, and the test was repeated at least three times. The CPE was monitored under a phase-contrast microscope at appropriate intervals for 24 h postinoculation.

For assessment of the level of cytotoxicity, a cell proliferation test using an MTT [3-(4,5-dimethyl-2-thiazolyl)-2, 5-diphenyl-2H tetrazolium bromide] assay as described in Behl (1992) and Heiss (1997) was conducted 24 h postinoculation by using a Premix™ WST-1 kit (Takara Co.). The average of absorbance in mock-inoculated negative controls was used as a blank value. The arbitrary unit was defined on the basis of the relative value of absorbance at 450 nm to the blank (1.0). The 50% effective concentrations (EC50s) were deduced from the dose-response curves using a log-probit program. Table 2 below presents the EC50s.

The protein exhibited cytotoxicity against HeLa, TCS, HL-60, Jurkat and Hep-G2 cells when treated with trypsin. No cytocidal activity was induced after treatment with chymotrypsin or proteinase K on HeLa, MOLT-4 and Sawano cells. Without protease digestion, inclusion proteins showed no cytocidal toxicity. Trypsin cleaves the cry31Aa2 protein after the arginine at position 250 of the full native protein sequence (SEQ ID NO: 2). The sequence of the trypsin-activated protein is designated SEQ ID NO: 8 and the corresponding nucleotide sequence is designated SEQ ID NO: 9.

Table 2 shows the results of one-dose assays of trypsin-activated Cry31Aa2 as compared to those of trypsin-activated Cry31Aa1 against several species of cultured cells. The toxicity spectrum of the protein from the recombinant Cry-B was similar to that of the protein of the wild strain M15. Both cloned proteins were highly or moderately cytocidal against HeLa, TCS, HL-60, Jurkat and Hep-G2 but were slightly toxic or nontoxic for normal T cells and for Sawano, UtSMC, MOLT-4, A549, MRC-5, HC, Caco-2 and the non human cells tested.

TABLE 2

Effective concentration 50 of trypsin-activated cry31Aa2 as compared to that of activated cry31Aa1 on various cells

| | | Organ | Cell | Cell type | EC50(ug/ml) Cry31Aa2 | EC50(ug/ml) Cry31Aa1 |
|---|---|---|---|---|---|---|
| 1 | Human | Uterus | HeLa | Cervix cancer | 0.30 | 0.23 |
| 2 | | | Sawano | Uterus cancer, adenocarcinoma | >10 | |
| 3 | | | TCS | Cervix cancer, keratinizing squamous | 0.32 | |
| 4 | | | UtSMC | Uterus normal smooth muscle | >10 | |

TABLE 2-continued

Effective concentration 50 of trypsin-activated cry31Aa2 as compared to that of activated cry31Aa1 on various cells

| | | Organ | Cell | Cell type | EC50(ug/ml) Cry31Aa2 | EC50(ug/ml) Cry31Aa1 |
|---|---|---|---|---|---|---|
| 5 | | Blood | MOLT-4 | T cell leukaemia | >10 | 1.06 |
| 6 | | | HL-60 | T cell leukaemia | 0.05 | |
| 7 | | | Jurkat | T cell leukaemia | 0.02 | |
| 8 | | | T cell | Normal T cell | >10 | |
| 9 | | Lung | A549 | Lung cancer | >10 | |
| 10 | | | MRC-5 | Lung normal fibroblast | >10 | |
| 11 | | Liver | HC | Normal hepatocyte cell | >10 | |
| 12 | | | Hep-G2 | Liver carcinoma hepatocellular | 0.02 | |
| 13 | | Colon | Caco-2 | Colon cancer, adenocarcinoma | >10 | |
| 14 | Monkey | Kidney | Vero | Monkey, kidney epithelial cell | >10 | |
| 15 | | | COS-7 | Monkey, kidney SV40 transformed cell | >10 | |
| 16 | Mouse | Embryo | NIH3T3 | Mouse, embryo fibroblast cell | >10 | |

Comparison of Cry31Aa2 and Cry31Aa1

As may be seen in FIG. 5, the Cry31Aa2 amino acid sequence shares extensive homology with Cry31Aa1 except for a substitution of 25 amino acid residues and an addition of 19 contiguous codons in cry31Aa2 (FIG. 5). This 19 amino acid sequence is as follows SYQNMKTEIVNT-DLPYNTN and is designated SEQ ID NO: 10 while the corresponding nucleotide sequence is designated SEQ ID NO: 11. The asterisks under the Cry31Aa2 sequence indicate the identities between Cry31Aa2 and Cry31Aa1. The capital letters and dotted lines under the amino acid sequence of Cry31Aa2 in FIG. 5, correspond to the difference and alignment gaps between the Cry31Aa2 and Cry31Aa1 proteins. The 83-KDa Cry31Aa2 protein exhibits 94% amino acid sequence identities with the Cry31Aa1 protein. The five conserved amino acid blocks of the Cry31Aa2 protein were especially identical to those of the Cry31Aa1 protein except for the substitution of a single lysine residue in the second conserved block of Cry31Aa2. The bold lines above the Cry31Aa2 sequence correspond to the five conserved amino acid blocks found in the amino acid sequence of cry31Aa1. Both Cry31Aa2 and Cry31Aa1 show very low amino acid sequence homology to the known *B. thuringiensis* Cry and Cyt proteins (Mizuki et al., 2000). The nucleotide sequence of the portion of the cry31Aa2 gene encoding the trypsin-activated protein shares a 98% identity with the corresponding sequence of cry31Aa1.

Table 2 above shows that both Cry31Aa2 and Cry31Aa1 protein display cytotoxicity against a number of human cancer cells. The cytocidal activity of the Cry31Aa1 was due to the cleavage by proteinase K and trypsin (Mizuki et al., 2000) while that of Cry31Aa2 was due to trypsin. The comparison of the amino acid sequence of Cry31Aa1 with that of Cry31Aa2 indicate which amino acids of the amino acid sequence of members of the Cry31 family can be substituted without abrogating this cytoxicity against human cancer cells. Although certain of these substitutions surely provide for the specificity of each of Cry31Aa2 and Cry31Aa1 against specific human cancer cells, they each display a significant toxicity against a number of human cancer cells. Hence, it is submitted that the amino acids at positions 24, 37, 39, 51, 56, 59, 87, 97, 138, 158, 170, 251, 389, 444-446, 466, 481, 507, 510, 518, 551, 582, 637, 725 and 742 can be replaced by any other amino acid without abrogating the cytotoxicity of the protein that it constitutes against at least some cancer cells. Sequences encompassing substitutions at these positions in the complete Cry31Aa2 protein sequence (SEQ ID NO: 2) and in the trypsin-activated Cry31Aa2 protein sequence (SEQ ID NO: 8) starting after the arginine at position 250 are within the scope of the present invention and are designated herein as SEQ ID NOs: 12 and 13, respectively.

Certain substitutions are preferred however and correspond to either a substitution by an amino acid having similar chemical properties or, even more preferred, a substitution by the amino acid found at the corresponding position in Cry31Aa1. Amino acids are categorized herein into 5 groups of amino acids according to their chemical properties, namely small nonpolar (i.e. C, P, A and T), small polar (i.e. S, G, D and N), large polar (i.e. E, Q, K and R), intermediate polarity (i.e. Y, H and W), aand large nonpolar (i.e. F, M, L, I and V). Hence, the amino acid at position 24 of the Cry31Aa2, is preferably a polar amino acid, most preferably a large polar amino acid and even more preferably glutamate or lysine. The amino acid at position 37 is preferably methionine or alanine. The amino acid at position 39 is preferably threonine or asparagine. The amino acid at position 51, is preferably a nonpolar amino acid, most preferably a small nonpolar amino acid and even more preferably alanine or threonine. The amino acid at position 56 is preferably proline or serine. The amino acid at position 59 is preferably an amino acid of intermediate polarity and most preferably tyrosine or tryptophan. The amino acid at position 87, is preferably a polar amino acid, most preferably a small polar amino acid and even more preferably asparagine or aspartate. The amino acid at position 97, is preferably a polar amino acid, most preferably a large polar amino acid and even most preferably arginine or lysine. The amino acid at position 138 is preferably a polar amino acid, most preferably a large polar amino acid and even more preferably glutamate or lysine. The amino acid at position 158 is preferably alanine or asparagine. The amino acid at position 170 is preferably a polar amino acid, most preferably a small polar amino acid and even more preferably glycine or serine.

The amino acid at position 251 is preferably a nonpolar amino acid, most preferably a large nonpolar amino acid and even more preferably isoleucine or methionine. The amino acid at position 389 is preferably a polar amino acid, most preferably a large polar amino acid and even more preferably lysine or arginine. The amino acid at position 444 is preferably serine or histidine. The amino acid at position 445 is preferably a polar amino acid, most preferably a small polar amino acid and even more preferably glycine or serine.

The amino acid at position 446 is preferably glycine or proline. The amino acid at position 466 is preferably a polar amino acid, most preferably a large polar amino acid and even more preferably glutamine or arginine. The amino acid at position 481 is preferably an amino acid of intermediate polarity and most preferably tyrosine or tryptophan. The amino acid at position 507 is preferably alanine or leucine. The amino acid at position 510 is preferably glycine or histidine. The amino acid at position 518 is preferably a nonpolar amino acid and is preferably alanine or valine. The amino acid at position 551 is preferably a nonpolar amino acid, most preferably a small nonpolar amino acid and even more preferably alanine or proline. The amino acid at position 582 is preferably a nonpolar amino acid, most preferably a small nonpolar amino acid and even more preferably alanine or threonine. The amino acid at position 637 is preferably arginine or isoleucine. The amino acid at position 725 is preferably glycine or arginine. Finally, the amino acid at position 742 is preferably valine or serine. Sequences encompassing the most preferred substitutions listed above at these positions in the complete Cry31Aa2 protein sequence (SEQ ID NO: 2) and in the trypsin-activated Cry31Aa2 protein sequence (SEQ ID NO: 8) starting after the arginine at position 250 are within the scope of the present invention and are designated herein as SEQ ID NOs: 14 and 15, respectively Sequences encompassing all the possible substitutions to the cry31Aa2 gene nucleotide sequence, the crystal protein and the trypsin-activated crystal protein derived from the crystal protein of the *Bacillus thuringiensis* M15 deposited under no. IDAC010201-5 as described above are within the scope of the present invention.

Although the present invention has been described hereinabove by way of preferred embodiments thereof, it can be modified, without departing from the spirit and nature of the subject invention as defined in the appended claims.

References

1. Aronson, A. (1993). The two faces of *Bacillus thuringiensis*: insecticidal proteins and post-exponential survival. Mol. Microbiol. 7, 489-496.
2. Baum, J. A., and Malvar, T. (1995). Regulation of insecticidal crystal protein production in *Bacillus thuringiensis. Mol. Microbiol.* 18,1-12.
3. Behl, C., J. Davis, G. M. Cole, and D. Schubert. 1992. Vitamin E protects nerve cells from amyloid protein toxicity. *Biochem. Biophys. Res. Commun.* 186:944-950.
4. Beveridge, T. J., Popkin, T. J., and Cole, R. M. (1994). Electron microscopy. In "Methods for General and Molecular Bacteriology" (Gerhardt, P., R. G. E. Murray, W. A. Wood, and N. R. Krieg, Eds.), pp. 42-71. Washington, D.C. Am. Soc. for Microbiol.
5. Birnboim, H. C., and Doly, J. (1979). A rapid alkaline extraction procedure for screening recombinant plasmid DNA. *Nucleic Acids Res.* 7, 1513-1523.
6. Crickmore, N. 2001. *Bacillus thuringiensis* toxin gene nomenclature. Web site http://epunix. biols. susx. ac. uk/Home/Neil_Crickmore/Bt/index.html.
7. Crickmore, N., Zeigler, D. R., Feitelson, J., Schnepf, E., Van Rie, J., Lereclus, D., Baum, J., and Dean, D. H. (1998). Revision of the nomenclature for the *Bacillus thuringiensis* pesticidal crystal proteins. *Microbiol. Mol. Biol. Rev.* 62, 807-813. de Barjac, H., and Frachon, E. (1990). Classification of *Bacillus thuringiensis* strains. *Entomophaga* 35, 233-240.
8. Feitelson, J. S., Payne, J., and Kim, L. (1992). *Bacillus thuringiensis*: insects and beyond. *Bio/Technology* 10, 271-275.
9. Gill, S. S., Cowles, E. A., and Pietrantonio, P. V. (1992). The mode of action of *B. thuringiensis* endotoxins. *Annu. Rev. Entomol.* 37, 615-636.
10. Goodman, N. S., R. J. Gottfried, and M. H. Rogoff. 1967. Biphasic system for separation of spores and crystals of *Bacillus thuringiensis. J. Bacteriol.* 94:485
11. Haima, P., Van Sinderen, D., Schotting, H., Bron, S., and Venema, G. (1990). Development of a β-galactosidase α-complementation system for molecular cloning in *Bacillus subtilis. Gene* 86, 63-69.
12. Heiss, P., S. Bernatz, G. Bruchelt, and R. Senekowitsch-Schmidtke. 1997. Cytotoxic effect of immunoconjugate composed of glucose-oxidase coupled to an anti-ganglioside ($G_{D2}$) antibody on spheroids. *Anticancer Res.* 17:3177-3178
13. Höfte, H., and Whiteley, H. R. (1989). Insecticidal crystal proteins of *B. thuringiensis. Microbiol. Rev.* 53, 242-255.
14. Jung, Y. C., Kim, S. U., Côté, J. -C., Lecadet, M. -M., and Chung, Y. S., and Bok, S. H. (1998). Characterization of a new *Bacillus thuringiensis* subsp. *higo* strain isolated from rice bran in Korea. *J. Invertebr. Pathol.* 71, 95-96.
15. Kim, H. S. (2000). Comparative study of the frequency, flagellar serotype, crystal shape, toxicity, and cry gene contents of *Bacillus thuringiensis* from three environments. *Curr. Microbiol.* 41, 250-256.
16. Laemmli, U. K., and Favre, M. (1973). Maturation of the head of acteriophage T4. *J. Mol. Biol.* 80, 575-599.
17. Lecadet, M. -M., Frachon, E., Cosmao Dumanoir, V. et al. (1999). Updating the H-antigen classification of *Bacillus thuringiensis. J. Appl. Microbiol.* 86, 660-672.
18. Lee, D. W., Akao, T., Yamashita, S., Katayama, H., Maeda, M., Saitoh, H., Mizuki, E., and Ohba, M. (2000). Noninsecticidal parasporal proteins of a *Bacillus thuringiensis* serovar *shandongiensis* isolate exhibit a preferential cytotoxicity against human leukemic T cells. *Biochem. Biophys. Res. Commun.* 272, 218-223.
19. Lereclus, D., Bourgouin, C., Lecadet, M. -M., Klier, A., and Rapoport,.G. (1989). Role, structure, and molecular organization of the genes coding for the parasporal δ-endotoxins of *B. thuringiensis*. In "Regulation of Procaryotic Development: Structural and Functional Analysis of Bacterial Sporulation and Germination" (Smith, I., R. A. Slepecky, and P. Setlow, Eds.), pp. 255-276, Washington, D.C. Am. Soc. for Microbiol.
20. McLaughlin, J. R., Murray, C. L., and Rabinowitz, J. C. (1981). Unique features in the ribosome binding site sequence of the Gram-positive *Staphylococcus aureus* β-lactamase gene. *J. Biol. Chem.* 256, 11283-11291.
21. Mizuki, E., Ohba, M., Akao, T., Yamashita, S., Saitoh, H., and Park, Y. S. (1999). Unique activity associated with non-insecticidal *Bacillus thuringiensis* parasporal inclusions: in vitro cell-killing action on human cancer cells. *J. Appl. Microbiol.* 86, 477-486.
22. Mizuki, E., Park, Y. S., Saitoh, H., Yamashita, S., Akao, T., Higuchi, K., and Ohba, M. (2000). Parasporin, a human leukemic cell-recognizing parasporal protein of *Bacillus thuringiensis. Clin. Diag. Lab. Immunol.* 7, 625-634.
23. Moran, C. P., Lang, N., Jr., LeGrice, S. F. J., Lee, G., Stephens, M., Sonenshein, A. L., Pero, J., and Losick, R. (1982). Nucleotide sequences that signal the initiation of transcription and translation in *Bacillus subtilis. Mol Gen. Gene.* 186, 339-346.

24. Ohba, M. (1996). *Bacillus thuringiensis* populations naturally occuring on mulberry leaves: a possible source of the populations associated with silkworm-rearing insectaries. *J. Appl. Bacteriol.* 80, 56-64.

25. Ohba, M., and Aizawa, K. (1986). Insect toxicity of *Bacillus thuringiensis* isolated from soils of Japan. *J. Invertebr. Pathol.* 47,12-20.

26. Roh, J. Y., Park, H. W., Jin, B. R., Kim, H. S., Yu, Y. M., and Kang, S. K. (1996). Characterization of novel non-toxic *Bacillus thuringiensis* isolates from Korea. *Lett. Appl. Microbiol.* 23, 249-252.

27. Sambrook, J., Fritsch, E. F., and Maniatis, T. (1989). "Molecular cloning. A Laboratory manual," 2nd ed. Cold Spring Harbor Laboratory Press, Cold Spring Harbor, N.Y.

28. Saitoh, H., K. Higuchi, E. Mizuki, and M. Ohba. (1998a). Larvicidal toxicity of Japanese *Bacillus thuringiensis* against the mosquito *Anopheles stephensi. Med. Vet. Entomol.* 12:98-102.

29. Saitoh, H., K. Higuchi, E. Mizuki, S.-H. Hwang, and M. Ohba. (1998b). Characterization of mosquito larvicidal parasporal inclusions of a *Bacillus thuringiensis* serovar *higo* strain. *J. Appl. Microbiol.* 84:883-888

30. Schnepf, H. E., Wong, H. C., and Whiteley, H. R. (1985). The amino acid sequence of a crystal protein from *Bacillus thuringiensis* deduced from the DNA base sequence. *J. Biol. Chem.* 260, 6264-6272.

31. Southern, E. (1975). Detection of specific sequences among DNA fragments separated by gel electrophoresis. *J. Mol. Biol.* 98, 503-517.

32. Stahly, D. P., Dingman, D. W., Bulla, L. A., Jr., and Aronson, A. I. (1978). Possible origin and function of the parasporal crystal in *Bacillus thuringiensis. Biochem. Biophys. Res. Commun.* 84, 581-588.

33. Thomas, W. E., and Ellar, D. J. (1983). *B. thuringiensis* var. *israelensis* crystal δ-endotoxin: effects on insect and mammalian cells in vitro and in vivo. *J. Cell. Sci.* 60, 181-197.

34. Tinoco, I., Jr., Borer, P. N., Dengler, B., Levine, M. D., Uhlenbeck, O. C., Crothers, D. M., and Gralla, J. (1973). Improved estimation of secondary structure in ribonucleic acids. *Nature New Biol.* 246, 40-41.

35. Vehmaanperä, J. (1989). Transformation of *Bacillus amyloliquefaciens* by electroporation. *FEMS Microbiol. Lett.* 61, 165-170.

36. Jung, Y.-C. (2001) *Bacillus thuringiensis* Strain M15, a Novel Autoagglutinable, Non-Serotypeable Strain-Cloning and Characterization of a Novel cry31A-type Crystal Protein Gene, cry31Aa2, and Two New Insertion Sequences, IS231M and -N. Département de sciences biologiques, Faculté des arts et des sciences, Université de Montréal.

What is claimed is:

1. An isolated Cry31Aa polypeptide having cytotoxic activity against human cancer cells selected from the group consisting of Hela, Sawano, TCS, MOLT-4, HL-60, Jurkat, A549, Hep-G2 and Caco-2 cells, the polypeptide comprising a sequence having at least 97% identity with the amino acid sequence of SEQ ID NO: 8.

2. An isolated Cry31Aa polypeptide having cytotoxic activity aqainst human cancer cells selected from the group consisting of Hela, Sawano, TOS, MOLT4, HL-60, Jurkat, A549, Hep-G2 and Caco-2 cells, wherein said polypeptide comprises the amino acid sequence of SEQ ID NO: 13, with the proviso that the polypeptide does not comprise amino acids 232 to 723 of SEQ ID NO: 18.

3. The isolated polypeptide of claim 2, wherein said polypeptide comprises the amino acid sequence of SEQ ID NO: 8.

4. The isolated polypeptide of claim 1, wherein said polypeptide comprises the amino acid sequence of SEQ ID NO: 8.

5. The isolated polypeptide of claim 1, wherein said polypeptide consists of the amino acid sequence of SEQ ID NO: 8.

* * * * *

SEQUENCE LISTING

```
<160> NUMBER OF SEQ ID NOS: 18

<210> SEQ ID NO 1
<211> LENGTH: 2229
<212> TYPE: DNA
<213> ORGANISM: Bacillus thuringiensis

<400> SEQUENCE: 1

gtggacccat tttctaatta ttctgaacaa aaatacccag attcaaataa taaccaagaa      60

ctaattacag aatcctcttc attttattcg gatactacta atgaaaatat gaaaacttac     120

catccaattg aacaagatat tctcaaattt gcaaatcaag aatttcccga taattattat     180

caacattccg atgtttctaa ttcatatcaa aatatgaaaa cagaaatcgt aaatacagat     240

ttaccctata atacaaataa tataaatagt atgcgaaata ctctatgcag agatttacct     300

cccgagacta acatgagcat ttatgataat ttacgatcta ctgttactgt tccttcattt     360

tctaatcaat ttgatcctat aaaatttctt cacgatattg aaattgctat agaaactgga     420

tcattttctg cattaacgca atctaacatg aatcaaggtg gtactgatat tgctccaatg     480

ttaatctcta cattttttaa agttgcaggt agtttacttc catttcctct atcatcatta     540

ggtgctttgg cttcctttta tgttacagat tcacaaacag gcgctatggc aaatttatgg     600

agacaaatgg tagattatgt tgaaaaaaga attgattcta aaatattaga ttatcataat     660

tttattatgg gagcagaact cgcagcatta aatgcaagtt taaaagaata cgcacgagta     720

gttaaaattt ttgaaaatga tatgaacaga atagctgaac caccttcaac tggagttatc     780

actcaattca gaattcttaa tgataatttc attaaatata ttgcaaaatt acaattctca     840

acaaatcaat cagatttaca atatcctgtc ctaactttac cattacgtgc acaagcatgt     900

gtaatgcatt taatgttatt aaaagatgca acgacttctg tgtggggaca acaaatagac     960
```

-continued tcgcaacaat taaatgggta taaagcagaa ttaatacgtt taataaaagt atatactaat 1020
gatgtaaaca caacgtataa tcaagggcta gagctagaaa aagctaaacc actaaattat 1080
tctgatcctg aagaatattt acaagcagga cgtccagata tatctgtatt acgcagtaac 1140
tttaaagagg ttatgaagtg gaataaagta gcgaaatata aacgtggaat ggctatgagt 1200
gctttatcat tagctgcatt atttccaact ttcggaccaa attatccaaa acaagcatta 1260
aaagttgtgc aatctagaca aatttttgca cctgtaattg gaataccagg cggtataaca 1320
agtcaagata gtggtcccac ttttggtagt atgagatttg atgtaaaaac ttatgatcaa 1380
attgatgcgt tacgacaact aatggaatta tatattcaac ctttaaaatc tgcttacttt 1440
tggatatatg aatcggattg gaaagttcgt gcaacttatg tcaatgatta tattggtaaa 1500
agagggtcaa atacaggtgc tgcttggcac atgtggtcaa gtgatccttc agccatatac 1560
acttctgcac taggagcagc aggatacgct cctaacgttg ttggtgtaag atattcacat 1620
gggggtagtt acacaaaagg tatggcaccc gcaaatacta atgcgtatgc tccatttgaa 1680
tttaaatatc ctggttataa actacacagt gttagtgctt atggattaag taaagcacct 1740
gatgcagctg attctgttat gtttggattt agacctgtat tgttagaaaa tgaagcaaat 1800
caattattaa cagatacagc attgcaaatt ccagcagaaa taggaataac agatgtcgta 1860
cctgcatttg gtagaacaga agaacctatt aatggtcaag atgcaataag aatatgggaa 1920
agttttacaa gtggatttgg ctttacttat actgttgatt ctccacaaaa acaaaaatat 1980
aaaatcattt atagaattgc aaataactta agcgcttcta cagtttcttt aacctataat 2040
aatcaaacat ttttcactga tattttaaat acttcattag atccaaatgg agtaagagga 2100
aattatggtt cttatacact tgtagaaggt cctattattg aattttctca aggaactaat 2160
atctttaaac taggatcaca aaaaggagaa ttcgctatag attccattat ttttagtcct 2220
gttgtttaa 2229

<210> SEQ ID NO 2
<211> LENGTH: 742
<212> TYPE: PRT
<213> ORGANISM: Bacillus thuringiensis

<400> SEQUENCE: 2

Met Asp Pro Phe Ser Asn Tyr Ser Glu Gln Lys Tyr Pro Asp Ser Asn
1 5 10 15

Asn Asn Gln Glu Leu Ile Thr Glu Ser Ser Ser Phe Tyr Ser Asp Thr
20 25 30

Thr Asn Glu Asn Met Lys Thr Tyr His Pro Ile Glu Gln Asp Ile Leu
35 40 45

Lys Phe Ala Asn Gln Glu Phe Pro Asp Asn Tyr Tyr Gln His Ser Asp
50 55 60

Val Ser Asn Ser Tyr Gln Asn Met Lys Thr Glu Ile Val Asn Thr Asp
65 70 75 80

Leu Pro Tyr Asn Thr Asn Asn Ile Asn Ser Met Arg Asn Thr Leu Cys
85 90 95

Arg Asp Leu Pro Pro Glu Thr Asn Met Ser Ile Tyr Asp Asn Leu Arg
100 105 110

Ser Thr Val Thr Val Pro Ser Phe Ser Asn Gln Phe Asp Pro Ile Lys
115 120 125

Phe Leu His Asp Ile Glu Ile Ala Ile Glu Thr Gly Ser Phe Ser Ala
130 135 140

-continued

```
Leu Thr Gln Ser Asn Met Asn Gln Gly Gly Thr Asp Ile Ala Pro Met
145                 150                 155                 160

Leu Ile Ser Thr Phe Phe Lys Val Ala Gly Ser Leu Leu Pro Phe Pro
                165                 170                 175

Leu Ser Ser Leu Gly Ala Leu Ala Ser Phe Tyr Val Thr Asp Ser Gln
            180                 185                 190

Thr Gly Ala Met Ala Asn Leu Trp Arg Gln Met Val Asp Tyr Val Glu
        195                 200                 205

Lys Arg Ile Asp Ser Lys Ile Leu Asp Tyr His Asn Phe Ile Met Gly
    210                 215                 220

Ala Glu Leu Ala Ala Leu Asn Ala Ser Leu Lys Glu Tyr Ala Arg Val
225                 230                 235                 240

Val Lys Ile Phe Glu Asn Asp Met Asn Arg Ile Ala Glu Pro Pro Ser
                245                 250                 255

Thr Gly Val Ile Thr Gln Phe Arg Ile Leu Asn Asp Asn Phe Ile Lys
            260                 265                 270

Tyr Ile Ala Lys Leu Gln Phe Ser Thr Asn Gln Ser Asp Leu Gln Tyr
        275                 280                 285

Pro Val Leu Thr Leu Pro Leu Arg Ala Gln Ala Cys Val Met His Leu
    290                 295                 300

Met Leu Leu Lys Asp Ala Thr Thr Ser Val Trp Gly Gln Gln Ile Asp
305                 310                 315                 320

Ser Gln Gln Leu Asn Gly Tyr Lys Ala Glu Leu Ile Arg Leu Ile Lys
                325                 330                 335

Val Tyr Thr Asn Asp Val Asn Thr Thr Tyr Asn Gln Gly Leu Glu Leu
            340                 345                 350

Glu Lys Ala Lys Pro Leu Asn Tyr Ser Asp Pro Glu Glu Tyr Leu Gln
        355                 360                 365

Ala Gly Arg Pro Asp Ile Ser Val Leu Arg Ser Asn Phe Lys Glu Val
    370                 375                 380

Met Lys Trp Asn Lys Val Ala Lys Tyr Lys Arg Gly Met Ala Met Ser
385                 390                 395                 400

Ala Leu Ser Leu Ala Ala Leu Phe Pro Thr Phe Gly Pro Asn Tyr Pro
                405                 410                 415

Lys Gln Ala Leu Lys Val Val Gln Ser Arg Gln Ile Phe Ala Pro Val
            420                 425                 430

Ile Gly Ile Pro Gly Gly Ile Thr Ser Gln Asp Ser Gly Pro Thr Phe
        435                 440                 445

Gly Ser Met Arg Phe Asp Val Lys Thr Tyr Asp Gln Ile Asp Ala Leu
    450                 455                 460

Arg Gln Leu Met Glu Leu Tyr Ile Gln Pro Leu Lys Ser Ala Tyr Phe
465                 470                 475                 480

Trp Ile Tyr Glu Ser Asp Trp Lys Val Arg Ala Thr Tyr Val Asn Asp
                485                 490                 495

Tyr Ile Gly Lys Arg Gly Ser Asn Thr Gly Ala Ala Trp His Met Trp
            500                 505                 510

Ser Ser Asp Pro Ser Ala Ile Tyr Thr Ser Ala Leu Gly Ala Ala Gly
        515                 520                 525

Tyr Ala Pro Asn Val Val Gly Val Arg Tyr Ser His Gly Gly Ser Tyr
    530                 535                 540

Thr Lys Gly Met Ala Pro Ala Asn Thr Asn Ala Tyr Ala Pro Phe Glu
545                 550                 555                 560

Phe Lys Tyr Pro Gly Tyr Lys Leu His Ser Val Ser Ala Tyr Gly Leu
```

-continued

```
                565                 570                 575

Ser Lys Ala Pro Asp Ala Ala Asp Ser Val Met Phe Gly Phe Arg Pro
            580                 585                 590

Val Leu Leu Glu Asn Glu Ala Asn Gln Leu Leu Thr Asp Thr Ala Leu
        595                 600                 605

Gln Ile Pro Ala Glu Ile Gly Ile Thr Asp Val Val Pro Ala Phe Gly
    610                 615                 620

Arg Thr Glu Glu Pro Ile Asn Gly Gln Asp Ala Ile Arg Ile Trp Glu
625                 630                 635                 640

Ser Phe Thr Ser Gly Phe Gly Phe Thr Tyr Thr Val Asp Ser Pro Gln
                645                 650                 655

Lys Gln Lys Tyr Lys Ile Ile Tyr Arg Ile Ala Asn Asn Leu Ser Ala
            660                 665                 670

Ser Thr Val Ser Leu Thr Tyr Asn Asn Gln Thr Phe Phe Thr Asp Ile
        675                 680                 685

Leu Asn Thr Ser Leu Asp Pro Asn Gly Val Arg Gly Asn Tyr Gly Ser
    690                 695                 700

Tyr Thr Leu Val Glu Gly Pro Ile Ile Glu Phe Ser Gln Gly Thr Asn
705                 710                 715                 720

Ile Phe Lys Leu Gly Ser Gln Lys Gly Glu Phe Ala Ile Asp Ser Ile
                725                 730                 735

Ile Phe Ser Pro Val Val
            740


<210> SEQ ID NO 3
<211> LENGTH: 20
<212> TYPE: PRT
<213> ORGANISM: Bacillus thuringiensis

<400> SEQUENCE: 3

Met Asp Pro Phe Ser Asn Tyr Ser Glu Gln Lys Tyr Pro Asp Ser Asn
1               5                   10                  15

Asn Asn Gln Glu
            20


<210> SEQ ID NO 4
<211> LENGTH: 6
<212> TYPE: PRT
<213> ORGANISM: Bacillus thuringiensis

<400> SEQUENCE: 4

Glu Gln Lys Tyr Pro Asp
1               5


<210> SEQ ID NO 5
<211> LENGTH: 18
<212> TYPE: DNA
<213> ORGANISM: Bacillus thuringiensis
<220> FEATURE:
<221> NAME/KEY: misc_feature
<222> LOCATION: (15)..(15)
<223> OTHER INFORMATION: n is a, c, g, or t

<400> SEQUENCE: 5

garcaraart ayccngay                                                    18


<210> SEQ ID NO 6
<211> LENGTH: 9
<212> TYPE: DNA
<213> ORGANISM: Bacillus thuringiensis
```

-continued

<400> SEQUENCE: 6 gaaaggtgg 9

<210> SEQ ID NO 7
<211> LENGTH: 10
<212> TYPE: RNA
<213> ORGANISM: Bacillus subtilis

<400> SEQUENCE: 7
ucuuuccucc 10

<210> SEQ ID NO 8
<211> LENGTH: 492
<212> TYPE: PRT
<213> ORGANISM: Bacillus thuringiensis

<400> SEQUENCE: 8

```
Ile Ala Glu Pro Pro Ser Thr Gly Val Ile Thr Gln Phe Arg Ile Leu
1               5                   10                  15

Asn Asp Asn Phe Ile Lys Tyr Ile Ala Lys Leu Gln Phe Ser Thr Asn
            20                  25                  30

Gln Ser Asp Leu Gln Tyr Pro Val Leu Thr Leu Pro Leu Arg Ala Gln
        35                  40                  45

Ala Cys Val Met His Leu Met Leu Leu Lys Asp Ala Thr Thr Ser Val
    50                  55                  60

Trp Gly Gln Gln Ile Asp Ser Gln Gln Leu Asn Gly Tyr Lys Ala Glu
65                  70                  75                  80

Leu Ile Arg Leu Ile Lys Val Tyr Thr Asn Asp Val Asn Thr Thr Tyr
                85                  90                  95

Asn Gln Gly Leu Glu Leu Glu Lys Ala Lys Pro Leu Asn Tyr Ser Asp
            100                 105                 110

Pro Glu Glu Tyr Leu Gln Ala Gly Arg Pro Asp Ile Ser Val Leu Arg
        115                 120                 125

Ser Asn Phe Lys Glu Val Met Lys Trp Asn Lys Val Ala Lys Tyr Lys
    130                 135                 140

Arg Gly Met Ala Met Ser Ala Leu Ser Leu Ala Ala Leu Phe Pro Thr
145                 150                 155                 160

Phe Gly Pro Asn Tyr Pro Lys Gln Ala Leu Lys Val Val Gln Ser Arg
                165                 170                 175

Gln Ile Phe Ala Pro Val Ile Gly Ile Pro Gly Gly Ile Thr Ser Gln
            180                 185                 190

Asp Ser Gly Pro Thr Phe Gly Ser Met Arg Phe Asp Val Lys Thr Tyr
        195                 200                 205

Asp Gln Ile Asp Ala Leu Arg Gln Leu Met Glu Leu Tyr Ile Gln Pro
    210                 215                 220

Leu Lys Ser Ala Tyr Phe Trp Ile Tyr Glu Ser Asp Trp Lys Val Arg
225                 230                 235                 240

Ala Thr Tyr Val Asn Asp Tyr Ile Gly Lys Arg Gly Ser Asn Thr Gly
                245                 250                 255

Ala Ala Trp His Met Trp Ser Ser Asp Pro Ser Ala Ile Tyr Thr Ser
            260                 265                 270

Ala Leu Gly Ala Ala Gly Tyr Ala Pro Asn Val Val Gly Val Arg Tyr
        275                 280                 285

Ser His Gly Gly Ser Tyr Thr Lys Gly Met Ala Pro Ala Asn Thr Asn
    290                 295                 300
```

-continued

Ala Tyr Ala Pro Phe Glu Phe Lys Tyr Pro Gly Tyr Lys Leu His Ser
305 310 315 320

Val Ser Ala Tyr Gly Leu Ser Lys Ala Pro Asp Ala Ala Asp Ser Val
325 330 335

Met Phe Gly Phe Arg Pro Val Leu Leu Glu Asn Glu Ala Asn Gln Leu
340 345 350

Leu Thr Asp Thr Ala Leu Gln Ile Pro Ala Glu Ile Gly Ile Thr Asp
355 360 365

Val Val Pro Ala Phe Gly Arg Thr Glu Glu Pro Ile Asn Gly Gln Asp
370 375 380

Ala Ile Arg Ile Trp Glu Ser Phe Thr Ser Gly Phe Gly Phe Thr Tyr
385 390 395 400

Thr Val Asp Ser Pro Gln Lys Gln Lys Tyr Lys Ile Ile Tyr Arg Ile
405 410 415

Ala Asn Asn Leu Ser Ala Ser Thr Val Ser Leu Thr Tyr Asn Asn Gln
420 425 430

Thr Phe Phe Thr Asp Ile Leu Asn Thr Ser Leu Asp Pro Asn Gly Val
435 440 445

Arg Gly Asn Tyr Gly Ser Tyr Thr Leu Val Glu Gly Pro Ile Ile Glu
450 455 460

Phe Ser Gln Gly Thr Asn Ile Phe Lys Leu Gly Ser Gln Lys Gly Glu
465 470 475 480

Phe Ala Ile Asp Ser Ile Ile Phe Ser Pro Val Val
485 490

<210> SEQ ID NO 9
<211> LENGTH: 1479
<212> TYPE: DNA
<213> ORGANISM: Bacillus thuringiensis

<400> SEQUENCE: 9
atagctgaac caccttcaac tggagttatc actcaattca gaattcttaa tgataatttc 60
attaaatata ttgcaaaatt acaattctca acaaatcaat cagatttaca atatcctgtc 120
ctaactttac cattacgtgc acaagcatgt gtaatgcatt taatgttatt aaaagatgca 180
acgacttctg tgtggggaca acaaatagac tcgcaacaat taaatgggta taaagcagaa 240
ttaatacgtt taataaaagt atatactaat gatgtaaaca caacgtataa tcaagggcta 300
gagctagaaa aagctaaacc actaaattat tctgatcctg aagaatattt acaagcagga 360
cgtccagata tatctgtatt acgcagtaac tttaaagagg ttatgaagtg gaataaagta 420
gcgaaatata aacgtggaat ggctatgagt gctttatcat tagctgcatt atttccaact 480
ttcggaccaa attatccaaa acaagcatta aaagttgtgc aatctagaca aatttttgca 540
cctgtaattg gaataccagg cggtataaca agtcaagata gtggtcccac ttttggtagt 600
atgagatttg atgtaaaaac ttatgatcaa attgatgcgt tacgacaact aatggaatta 660
tatattcaac ctttaaaatc tgcttacttt tggatatatg aatcggattg gaaagttcgt 720
gcaacttatg tcaatgatta tattggtaaa agagggtcaa atacaggtgc tgcttggcac 780
atgtggtcaa gtgatccttc agccatatac acttctgcac taggagcagc aggatacgct 840
cctaacgttg ttggtgtaag atattcacat gggggtagtt acacaaaagg tatggcaccc 900
gcaaatacta atgcgtatgc tccatttgaa tttaaatatc ctggttataa actacacagt 960
gttagtgctt atggattaag taaagcacct gatgcagctg attctgttat gtttggattt 1020

-continued

```
agacctgtat tgttagaaaa tgaagcaaat caattattaa cagatacagc attgcaaatt   1080

ccagcagaaa taggaataac agatgtcgta cctgcatttg gtagaacaga agaacctatt   1140

aatggtcaag atgcaataag aatatgggaa agttttacaa gtggatttgg ctttacttat   1200

actgttgatt ctccacaaaa acaaaaatat aaaatcattt atagaattgc aaataactta   1260

agcgcttcta cagtttcttt aacctataat aatcaaacat ttttcactga tattttaaat   1320

acttcattag atccaaatgg agtaagagga aattatggtt cttatacact tgtagaaggt   1380

cctattattg aattttctca aggaactaat atctttaaac taggatcaca aaaaggagaa   1440

ttcgctatag attccattat ttttagtcct gttgtttaa                          1479


<210> SEQ ID NO 10
<211> LENGTH: 19
<212> TYPE: PRT
<213> ORGANISM: Bacillus thuringiensis

<400> SEQUENCE: 10

Ser Tyr Gln Asn Met Lys Thr Glu Ile Val Asn Thr Asp Leu Pro Tyr
1               5                   10                  15

Asn Thr Asn


<210> SEQ ID NO 11
<211> LENGTH: 57
<212> TYPE: DNA
<213> ORGANISM: Bacillus thuringiensis

<400> SEQUENCE: 11

tcatatcaaa atatgaaaac agaaatcgta aatacagatt taccctataa tacaaat        57


<210> SEQ ID NO 12
<211> LENGTH: 742
<212> TYPE: PRT
<213> ORGANISM: Bacillus thuringiensis
<220> FEATURE:
<221> NAME/KEY: MISC_FEATURE
<222> LOCATION: (24)..(24)
<223> OTHER INFORMATION: Xaa=any amino acid
<220> FEATURE:
<221> NAME/KEY: MISC_FEATURE
<222> LOCATION: (37)..(37)
<223> OTHER INFORMATION: Xaa=any amino acid
<220> FEATURE:
<221> NAME/KEY: MISC_FEATURE
<222> LOCATION: (39)..(39)
<223> OTHER INFORMATION: Xaa=any amino acid
<220> FEATURE:
<221> NAME/KEY: MISC_FEATURE
<222> LOCATION: (51)..(51)
<223> OTHER INFORMATION: Xaa=any amino acid
<220> FEATURE:
<221> NAME/KEY: MISC_FEATURE
<222> LOCATION: (56)..(56)
<223> OTHER INFORMATION: Xaa=any amino acid
<220> FEATURE:
<221> NAME/KEY: MISC_FEATURE
<222> LOCATION: (59)..(59)
<223> OTHER INFORMATION: Xaa-any amino acid
<220> FEATURE:
<221> NAME/KEY: MISC_FEATURE
<222> LOCATION: (87)..(87)
<223> OTHER INFORMATION: Xaa=any amino acid
<220> FEATURE:
<221> NAME/KEY: MISC_FEATURE
<222> LOCATION: (97)..(97)
<223> OTHER INFORMATION: Xaa=any amino acid
<220> FEATURE:
<221> NAME/KEY: MISC_FEATURE
<222> LOCATION: (138)..(138)
```

-continued

<223> OTHER INFORMATION: Xaa=any amino acid
<220> FEATURE:
<221> NAME/KEY: MISC_FEATURE
<222> LOCATION: (158)..(158)
<223> OTHER INFORMATION: Xaa=any amino acid
<220> FEATURE:
<221> NAME/KEY: MISC_FEATURE
<222> LOCATION: (170)..(170)
<223> OTHER INFORMATION: xaa= any amino acid
<220> FEATURE:
<221> NAME/KEY: MISC_FEATURE
<222> LOCATION: (251)..(251)
<223> OTHER INFORMATION: Xaa=any amino acid
<220> FEATURE:
<221> NAME/KEY: MISC_FEATURE
<222> LOCATION: (389)..(389)
<223> OTHER INFORMATION: Xaa=any amino acid
<220> FEATURE:
<221> NAME/KEY: MISC_FEATURE
<222> LOCATION: (444)..(444)
<223> OTHER INFORMATION: Xaa=any amino acid
<220> FEATURE:
<221> NAME/KEY: MISC_FEATURE
<222> LOCATION: (445)..(445)
<223> OTHER INFORMATION: Xaa=any amino acid
<220> FEATURE:
<221> NAME/KEY: MISC_FEATURE
<222> LOCATION: (446)..(446)
<223> OTHER INFORMATION: Xaa=any amino acid
<220> FEATURE:
<221> NAME/KEY: MISC_FEATURE
<222> LOCATION: (466)..(466)
<223> OTHER INFORMATION: Xaa=any amino acid
<220> FEATURE:
<221> NAME/KEY: MISC_FEATURE
<222> LOCATION: (481)..(481)
<223> OTHER INFORMATION: Xaa=any amino acid
<220> FEATURE:
<221> NAME/KEY: MISC_FEATURE
<222> LOCATION: (507)..(507)
<223> OTHER INFORMATION: Any amino acid
<220> FEATURE:
<221> NAME/KEY: MISC_FEATURE
<222> LOCATION: (510)..(510)
<223> OTHER INFORMATION: Xaa=any amino acid
<220> FEATURE:
<221> NAME/KEY: MISC_FEATURE
<222> LOCATION: (518)..(518)
<223> OTHER INFORMATION: Xaa= any amino acid
<220> FEATURE:
<221> NAME/KEY: MISC_FEATURE
<222> LOCATION: (551)..(551)
<223> OTHER INFORMATION: Xaa=any amino acid
<220> FEATURE:
<221> NAME/KEY: MISC_FEATURE
<222> LOCATION: (582)..(582)
<223> OTHER INFORMATION: Xaa=any amino acid
<220> FEATURE:
<221> NAME/KEY: MISC_FEATURE
<222> LOCATION: (637)..(637)
<223> OTHER INFORMATION: Xaa=any amino acid
<220> FEATURE:
<221> NAME/KEY: MISC_FEATURE
<222> LOCATION: (725)..(725)
<223> OTHER INFORMATION: Xaa=any amino acid
<220> FEATURE:
<221> NAME/KEY: MISC_FEATURE
<222> LOCATION: (742)..(742)
<223> OTHER INFORMATION: Xaa=any amino acid

<400> SEQUENCE: 12

```
Met Asp Pro Phe Ser Asn Tyr Ser Glu Gln Lys Tyr Pro Asp Ser Asn
1               5                   10                  15

Asn Asn Gln Glu Leu Ile Thr Xaa Ser Ser Ser Phe Tyr Ser Asp Thr
            20                  25                  30

Thr Asn Glu Asn Xaa Lys Xaa Tyr His Pro Ile Glu Gln Asp Ile Leu
```

-continued

```
        35                  40                  45

Lys Phe Xaa Asn Gln Glu Phe Xaa Asp Asn Xaa Tyr Gln His Ser Asp
    50                  55                  60

Val Ser Asn Ser Tyr Gln Asn Met Lys Thr Glu Ile Val Asn Thr Asp
65                  70                  75                  80

Leu Pro Tyr Asn Thr Asn Xaa Ile Asn Ser Met Arg Asn Thr Leu Cys
                85                  90                  95

Xaa Asp Leu Pro Pro Glu Thr Asn Met Ser Ile Tyr Asp Asn Leu Arg
            100                 105                 110

Ser Thr Val Thr Val Pro Ser Phe Ser Asn Gln Phe Asp Pro Ile Lys
        115                 120                 125

Phe Leu His Asp Ile Glu Ile Ala Ile Xaa Thr Gly Ser Phe Ser Ala
    130                 135                 140

Leu Thr Gln Ser Asn Met Asn Gln Gly Gly Thr Asp Ile Xaa Pro Met
145                 150                 155                 160

Leu Ile Ser Thr Phe Phe Lys Val Ala Xaa Ser Leu Leu Pro Phe Pro
                165                 170                 175

Leu Ser Ser Leu Gly Ala Leu Ala Ser Phe Tyr Val Thr Asp Ser Gln
            180                 185                 190

Thr Gly Ala Met Ala Asn Leu Trp Arg Gln Met Val Asp Tyr Val Glu
        195                 200                 205

Lys Arg Ile Asp Ser Lys Ile Leu Asp Tyr His Asn Phe Ile Met Gly
    210                 215                 220

Ala Glu Leu Ala Ala Leu Asn Ala Ser Leu Lys Glu Tyr Ala Arg Val
225                 230                 235                 240

Val Lys Ile Phe Glu Asn Asp Met Asn Arg Xaa Ala Glu Pro Pro Ser
                245                 250                 255

Thr Gly Val Ile Thr Gln Phe Arg Ile Leu Asn Asp Asn Phe Ile Lys
            260                 265                 270

Tyr Ile Ala Lys Leu Gln Phe Ser Thr Asn Gln Ser Asp Leu Gln Tyr
        275                 280                 285

Pro Val Leu Thr Leu Pro Leu Arg Ala Gln Ala Cys Val Met His Leu
    290                 295                 300

Met Leu Leu Lys Asp Ala Thr Thr Ser Val Trp Gly Gln Gln Ile Asp
305                 310                 315                 320

Ser Gln Gln Leu Asn Gly Tyr Lys Ala Glu Leu Ile Arg Leu Ile Lys
                325                 330                 335

Val Tyr Thr Asn Asp Val Asn Thr Thr Tyr Asn Gln Gly Leu Glu Leu
            340                 345                 350

Glu Lys Ala Lys Pro Leu Asn Tyr Ser Asp Pro Glu Glu Tyr Leu Gln
        355                 360                 365

Ala Gly Arg Pro Asp Ile Ser Val Leu Arg Ser Asn Phe Lys Glu Val
    370                 375                 380

Met Lys Trp Asn Xaa Val Ala Lys Tyr Lys Arg Gly Met Ala Met Ser
385                 390                 395                 400

Ala Leu Ser Leu Ala Ala Leu Phe Pro Thr Phe Gly Pro Asn Tyr Pro
                405                 410                 415

Lys Gln Ala Leu Lys Val Val Gln Ser Arg Gln Ile Phe Ala Pro Val
            420                 425                 430

Ile Gly Ile Pro Gly Gly Ile Thr Ser Gln Asp Xaa Xaa Xaa Thr Phe
        435                 440                 445

Gly Ser Met Arg Phe Asp Val Lys Thr Tyr Asp Gln Ile Asp Ala Leu
    450                 455                 460
```

-continued

```
Arg Xaa Leu Met Glu Leu Tyr Ile Gln Pro Leu Lys Ser Ala Tyr Phe
465                 470                 475                 480

Xaa Ile Tyr Glu Ser Asp Trp Lys Val Arg Ala Thr Tyr Val Asn Asp
                485                 490                 495

Tyr Ile Gly Lys Arg Gly Ser Asn Thr Gly Xaa Ala Trp Xaa Met Trp
            500                 505                 510

Ser Ser Asp Pro Ser Xaa Ile Tyr Thr Ser Ala Leu Gly Ala Ala Gly
        515                 520                 525

Tyr Ala Pro Asn Val Val Gly Val Arg Tyr Ser His Gly Gly Ser Tyr
    530                 535                 540

Thr Lys Gly Met Ala Pro Xaa Asn Thr Asn Ala Tyr Ala Pro Phe Glu
545                 550                 555                 560

Phe Lys Tyr Pro Gly Tyr Lys Leu His Ser Val Ser Ala Tyr Gly Leu
                565                 570                 575

Ser Lys Ala Pro Asp Xaa Ala Asp Ser Val Met Phe Gly Phe Arg Pro
            580                 585                 590

Val Leu Leu Glu Asn Glu Ala Asn Gln Leu Leu Thr Asp Thr Ala Leu
        595                 600                 605

Gln Ile Pro Ala Glu Ile Gly Ile Thr Asp Val Val Pro Ala Phe Gly
    610                 615                 620

Arg Thr Glu Glu Pro Ile Asn Gly Gln Asp Ala Ile Xaa Ile Trp Glu
625                 630                 635                 640

Ser Phe Thr Ser Gly Phe Gly Phe Thr Tyr Thr Val Asp Ser Pro Gln
                645                 650                 655

Lys Gln Lys Tyr Lys Ile Ile Tyr Arg Ile Ala Asn Asn Leu Ser Ala
            660                 665                 670

Ser Thr Val Ser Leu Thr Tyr Asn Asn Gln Thr Phe Phe Thr Asp Ile
        675                 680                 685

Leu Asn Thr Ser Leu Asp Pro Asn Gly Val Arg Gly Asn Tyr Gly Ser
    690                 695                 700

Tyr Thr Leu Val Glu Gly Pro Ile Ile Glu Phe Ser Gln Gly Thr Asn
705                 710                 715                 720

Ile Phe Lys Leu Xaa Ser Gln Lys Gly Glu Phe Ala Ile Asp Ser Ile
                725                 730                 735

Ile Phe Ser Pro Val Xaa
            740
```

<210> SEQ ID NO 13
<211> LENGTH: 492
<212> TYPE: PRT
<213> ORGANISM: Bacillus thuringiensis
<220> FEATURE:
<221> NAME/KEY: MISC_FEATURE
<222> LOCATION: (1)..(1)
<223> OTHER INFORMATION: Xaa=any amino acid
<220> FEATURE:
<221> NAME/KEY: MISC_FEATURE
<222> LOCATION: (139)..(139)
<223> OTHER INFORMATION: Xaa=any amino acid
<220> FEATURE:
<221> NAME/KEY: MISC_FEATURE
<222> LOCATION: (194)..(194)
<223> OTHER INFORMATION: Xaa=any amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: MISC_FEATURE
<222> LOCATION: (216)..(216)

-continued

```
<223> OTHER INFORMATION: Xaa=any amino acid
<220> FEATURE:
<221> NAME/KEY: MISC_FEATURE
<222> LOCATION: (231)..(231)
<223> OTHER INFORMATION: Xaa=any amino acid
<220> FEATURE:
<221> NAME/KEY: MISC_FEATURE
<222> LOCATION: (257)..(257)
<223> OTHER INFORMATION: Xaa=any amino acid
<220> FEATURE:
<221> NAME/KEY: MISC_FEATURE
<222> LOCATION: (260)..(260)
<223> OTHER INFORMATION: Xaa=any amino acid
<220> FEATURE:
<221> NAME/KEY: MISC_FEATURE
<222> LOCATION: (268)..(268)
<223> OTHER INFORMATION: Xaa=any amino acid
<220> FEATURE:
<221> NAME/KEY: MISC_FEATURE
<222> LOCATION: (301)..(301)
<223> OTHER INFORMATION: Xaa=any amino acid
<220> FEATURE:
<221> NAME/KEY: MISC_FEATURE
<222> LOCATION: (332)..(332)
<223> OTHER INFORMATION: Xaa=any amino acid
<220> FEATURE:
<221> NAME/KEY: MISC_FEATURE
<222> LOCATION: (387)..(387)
<223> OTHER INFORMATION: Xaa=any amino acid
<220> FEATURE:
<221> NAME/KEY: MISC_FEATURE
<222> LOCATION: (475)..(475)
<223> OTHER INFORMATION: Xaa=any amino acid
<220> FEATURE:
<221> NAME/KEY: MISC_FEATURE
<222> LOCATION: (492)..(492)
<223> OTHER INFORMATION: Xaa=any amino acid

<400> SEQUENCE: 13

Xaa Ala Glu Pro Pro Ser Thr Gly Val Ile Thr Gln Phe Arg Ile Leu
1               5                   10                  15

Asn Asp Asn Phe Ile Lys Tyr Ile Ala Lys Leu Gln Phe Ser Thr Asn
            20                  25                  30

Gln Ser Asp Leu Gln Tyr Pro Val Leu Thr Leu Pro Leu Arg Ala Gln
        35                  40                  45

Ala Cys Val Met His Leu Met Leu Leu Lys Asp Ala Thr Thr Ser Val
    50                  55                  60

Trp Gly Gln Gln Ile Asp Ser Gln Gln Leu Asn Gly Tyr Lys Ala Glu
65                  70                  75                  80

Leu Ile Arg Leu Ile Lys Val Tyr Thr Asn Asp Val Asn Thr Thr Tyr
                85                  90                  95

Asn Gln Gly Leu Glu Leu Glu Lys Ala Lys Pro Leu Asn Tyr Ser Asp
            100                 105                 110

Pro Glu Glu Tyr Leu Gln Ala Gly Arg Pro Asp Ile Ser Val Leu Arg
        115                 120                 125

Ser Asn Phe Lys Glu Val Met Lys Trp Asn Xaa Val Ala Lys Tyr Lys
    130                 135                 140

Arg Gly Met Ala Met Ser Ala Leu Ser Leu Ala Ala Leu Phe Pro Thr
145                 150                 155                 160

Phe Gly Pro Asn Tyr Pro Lys Gln Ala Leu Lys Val Val Gln Ser Arg
                165                 170                 175

Gln Ile Phe Ala Pro Val Ile Gly Ile Pro Gly Gly Ile Thr Ser Gln
            180                 185                 190

Asp Xaa Xaa Xaa Thr Phe Gly Ser Met Arg Phe Asp Val Lys Thr Tyr
        195                 200                 205
```

-continued

```
Asp Gln Ile Asp Ala Leu Arg Xaa Leu Met Glu Leu Tyr Ile Gln Pro
    210                 215                 220

Leu Lys Ser Ala Tyr Phe Xaa Ile Tyr Glu Ser Asp Trp Lys Val Arg
225                 230                 235                 240

Ala Thr Tyr Val Asn Asp Tyr Ile Gly Lys Arg Gly Ser Asn Thr Gly
                245                 250                 255

Xaa Ala Trp Xaa Met Trp Ser Ser Asp Pro Ser Xaa Ile Tyr Thr Ser
            260                 265                 270

Ala Leu Gly Ala Ala Gly Tyr Ala Pro Asn Val Val Gly Val Arg Tyr
        275                 280                 285

Ser His Gly Gly Ser Tyr Thr Lys Gly Met Ala Pro Xaa Asn Thr Asn
    290                 295                 300

Ala Tyr Ala Pro Phe Glu Phe Lys Tyr Pro Gly Tyr Lys Leu His Ser
305                 310                 315                 320

Val Ser Ala Tyr Gly Leu Ser Lys Ala Pro Asp Xaa Ala Asp Ser Val
                325                 330                 335

Met Phe Gly Phe Arg Pro Val Leu Leu Glu Asn Glu Ala Asn Gln Leu
            340                 345                 350

Leu Thr Asp Thr Ala Leu Gln Ile Pro Ala Glu Ile Gly Ile Thr Asp
        355                 360                 365

Val Val Pro Ala Phe Gly Arg Thr Glu Glu Pro Ile Asn Gly Gln Asp
    370                 375                 380

Ala Ile Xaa Ile Trp Glu Ser Phe Thr Ser Gly Phe Gly Phe Thr Tyr
385                 390                 395                 400

Thr Val Asp Ser Pro Gln Lys Gln Lys Tyr Lys Ile Ile Tyr Arg Ile
                405                 410                 415

Ala Asn Asn Leu Ser Ala Ser Thr Val Ser Leu Thr Tyr Asn Asn Gln
            420                 425                 430

Thr Phe Phe Thr Asp Ile Leu Asn Thr Ser Leu Asp Pro Asn Gly Val
        435                 440                 445

Arg Gly Asn Tyr Gly Ser Tyr Thr Leu Val Glu Gly Pro Ile Ile Glu
    450                 455                 460

Phe Ser Gln Gly Thr Asn Ile Phe Lys Leu Xaa Ser Gln Lys Gly Glu
465                 470                 475                 480

Phe Ala Ile Asp Ser Ile Ile Phe Ser Pro Val Xaa
                485                 490
```

<210> SEQ ID NO 14
<211> LENGTH: 742
<212> TYPE: PRT
<213> ORGANISM: Bacillus thuringiensis
<220> FEATURE:
<221> NAME/KEY: MISC_FEATURE
<222> LOCATION: (24)..(24)
<223> OTHER INFORMATION: Xaa=glutamate or lysine
<220> FEATURE:
<221> NAME/KEY: MISC_FEATURE
<222> LOCATION: (37)..(37)
<223> OTHER INFORMATION: Xaa= methionine or alanine
<220> FEATURE:
<221> NAME/KEY: MISC_FEATURE
<222> LOCATION: (39)..(39)
<223> OTHER INFORMATION: Xaa= threonine or asparagine
<220> FEATURE:
<221> NAME/KEY: MISC_FEATURE
<222> LOCATION: (51)..(51)
<223> OTHER INFORMATION: Xaa= alanine or threonine
<220> FEATURE:
<221> NAME/KEY: MISC_FEATURE
<222> LOCATION: (56)..(56)
<223> OTHER INFORMATION: Xaa= proline or serine -continued
<220> FEATURE:
<221> NAME/KEY: MISC_FEATURE
<222> LOCATION: (59)..(59)
<223> OTHER INFORMATION: Xaa= tyrosine or tryptophan
<220> FEATURE:
<221> NAME/KEY: MISC_FEATURE
<222> LOCATION: (87)..(87)
<223> OTHER INFORMATION: Xaa= asparagine or aspartate
<220> FEATURE:
<221> NAME/KEY: MISC_FEATURE
<222> LOCATION: (97)..(97)
<223> OTHER INFORMATION: Xaa= arginine or lysine
<220> FEATURE:
<221> NAME/KEY: MISC_FEATURE
<222> LOCATION: (138)..(138)
<223> OTHER INFORMATION: Xaa= glutamate or lysine
<220> FEATURE:
<221> NAME/KEY: MISC_FEATURE
<222> LOCATION: (158)..(158)
<223> OTHER INFORMATION: Xaa= alanine or asparagine
<220> FEATURE:
<221> NAME/KEY: MISC_FEATURE
<222> LOCATION: (170)..(170)
<223> OTHER INFORMATION: Xaa= glycine or serine
<220> FEATURE:
<221> NAME/KEY: MISC_FEATURE
<222> LOCATION: (251)..(251)
<223> OTHER INFORMATION: Xaa= isoleucine or methionine
<220> FEATURE:
<221> NAME/KEY: MISC_FEATURE
<222> LOCATION: (389)..(389)
<223> OTHER INFORMATION: Xaa= lysine or arginine
<220> FEATURE:
<221> NAME/KEY: MISC_FEATURE
<222> LOCATION: (444)..(444)
<223> OTHER INFORMATION: xaa= serine or histidine
<220> FEATURE:
<221> NAME/KEY: MISC_FEATURE
<222> LOCATION: (445)..(445)
<223> OTHER INFORMATION: xaa= glycine or serine
<220> FEATURE:
<221> NAME/KEY: MISC_FEATURE
<222> LOCATION: (446)..(446)
<223> OTHER INFORMATION: Xaa= glycine or proline
<220> FEATURE:
<221> NAME/KEY: MISC_FEATURE
<222> LOCATION: (466)..(466)
<223> OTHER INFORMATION: Xaa= glutamine or arginine
<220> FEATURE:
<221> NAME/KEY: MISC_FEATURE
<222> LOCATION: (481)..(481)
<223> OTHER INFORMATION: Xaa= tyrosine or tryptophan
<220> FEATURE:
<221> NAME/KEY: MISC_FEATURE
<222> LOCATION: (507)..(507)
<223> OTHER INFORMATION: Xaa= alanine or leucine
<220> FEATURE:
<221> NAME/KEY: MISC_FEATURE
<222> LOCATION: (510)..(510)
<223> OTHER INFORMATION: Xaa= glycine or histidine
<220> FEATURE:
<221> NAME/KEY: MISC_FEATURE
<222> LOCATION: (518)..(518)
<223> OTHER INFORMATION: Xaa= alamine or valine
<220> FEATURE:
<221> NAME/KEY: MISC_FEATURE
<222> LOCATION: (551)..(551)
<223> OTHER INFORMATION: xaa= alanine or proline
<220> FEATURE:
<221> NAME/KEY: MISC_FEATURE
<222> LOCATION: (582)..(582)
<223> OTHER INFORMATION: Xaa= alanine or threonine
<220> FEATURE:
<221> NAME/KEY: MISC_FEATURE
<222> LOCATION: (637)..(637)
<223> OTHER INFORMATION: Xaa= arginine or isoleucine
<220> FEATURE:
<221> NAME/KEY: MISC_FEATURE
<222> LOCATION: (725)..(725)

-continued

<223> OTHER INFORMATION: Xaa= glycine or arginine
<220> FEATURE:
<221> NAME/KEY: MISC_FEATURE
<222> LOCATION: (742)..(742)
<223> OTHER INFORMATION: Xaa= valine or serine

<400> SEQUENCE: 14

```
Met Asp Pro Phe Ser Asn Tyr Ser Glu Gln Lys Tyr Pro Asp Ser Asn
1               5                   10                  15

Asn Asn Gln Glu Leu Ile Thr Xaa Ser Ser Ser Phe Tyr Ser Asp Thr
            20                  25                  30

Thr Asn Glu Asn Xaa Lys Xaa Tyr His Pro Ile Glu Gln Asp Ile Leu
        35                  40                  45

Lys Phe Xaa Asn Gln Glu Phe Xaa Asp Asn Xaa Tyr Gln His Ser Asp
    50                  55                  60

Val Ser Asn Ser Tyr Gln Asn Met Lys Thr Glu Ile Val Asn Thr Asp
65                  70                  75                  80

Leu Pro Tyr Asn Thr Asn Xaa Ile Asn Ser Met Arg Asn Thr Leu Cys
                85                  90                  95

Xaa Asp Leu Pro Pro Glu Thr Asn Met Ser Ile Tyr Asp Asn Leu Arg
            100                 105                 110

Ser Thr Val Thr Val Pro Ser Phe Ser Asn Gln Phe Asp Pro Ile Lys
        115                 120                 125

Phe Leu His Asp Ile Glu Ile Ala Ile Xaa Thr Gly Ser Phe Ser Ala
    130                 135                 140

Leu Thr Gln Ser Asn Met Asn Gln Gly Gly Thr Asp Ile Xaa Pro Met
145                 150                 155                 160

Leu Ile Ser Thr Phe Phe Lys Val Ala Xaa Ser Leu Leu Pro Phe Pro
                165                 170                 175

Leu Ser Ser Leu Gly Ala Leu Ala Ser Phe Tyr Val Thr Asp Ser Gln
            180                 185                 190

Thr Gly Ala Met Ala Asn Leu Trp Arg Gln Met Val Asp Tyr Val Glu
        195                 200                 205

Lys Arg Ile Asp Ser Lys Ile Leu Asp Tyr His Asn Phe Ile Met Gly
    210                 215                 220

Ala Glu Leu Ala Ala Leu Asn Ala Ser Leu Lys Glu Tyr Ala Arg Val
225                 230                 235                 240

Val Lys Ile Phe Glu Asn Asp Met Asn Arg Xaa Ala Glu Pro Pro Ser
                245                 250                 255

Thr Gly Val Ile Thr Gln Phe Arg Ile Leu Asn Asp Asn Phe Ile Lys
            260                 265                 270

Tyr Ile Ala Lys Leu Gln Phe Ser Thr Asn Gln Ser Asp Leu Gln Tyr
        275                 280                 285

Pro Val Leu Thr Leu Pro Leu Arg Ala Gln Ala Cys Val Met His Leu
    290                 295                 300

Met Leu Leu Lys Asp Ala Thr Thr Ser Val Trp Gly Gln Gln Ile Asp
305                 310                 315                 320

Ser Gln Gln Leu Asn Gly Tyr Lys Ala Glu Leu Ile Arg Leu Ile Lys
                325                 330                 335

Val Tyr Thr Asn Asp Val Asn Thr Thr Tyr Asn Gln Gly Leu Glu Leu
            340                 345                 350

Glu Lys Ala Lys Pro Leu Asn Tyr Ser Asp Pro Glu Glu Tyr Leu Gln
        355                 360                 365

Ala Gly Arg Pro Asp Ile Ser Val Leu Arg Ser Asn Phe Lys Glu Val
    370                 375                 380
```

-continued

```
Met Lys Trp Asn Xaa Val Ala Lys Tyr Lys Arg Gly Met Ala Met Ser
385                 390                 395                 400

Ala Leu Ser Leu Ala Ala Leu Phe Pro Thr Phe Gly Pro Asn Tyr Pro
                405                 410                 415

Lys Gln Ala Leu Lys Val Val Gln Ser Arg Gln Ile Phe Ala Pro Val
            420                 425                 430

Ile Gly Ile Pro Gly Gly Ile Thr Ser Gln Asp Xaa Xaa Xaa Thr Phe
        435                 440                 445

Gly Ser Met Arg Phe Asp Val Lys Thr Tyr Asp Gln Ile Asp Ala Leu
    450                 455                 460

Arg Xaa Leu Met Glu Leu Tyr Ile Gln Pro Leu Lys Ser Ala Tyr Phe
465                 470                 475                 480

Xaa Ile Tyr Glu Ser Asp Trp Lys Val Arg Ala Thr Tyr Val Asn Asp
                485                 490                 495

Tyr Ile Gly Lys Arg Gly Ser Asn Thr Gly Xaa Ala Trp Xaa Met Trp
            500                 505                 510

Ser Ser Asp Pro Ser Xaa Ile Tyr Thr Ser Ala Leu Gly Ala Ala Gly
        515                 520                 525

Tyr Ala Pro Asn Val Val Gly Val Arg Tyr Ser His Gly Gly Ser Tyr
    530                 535                 540

Thr Lys Gly Met Ala Pro Xaa Asn Thr Asn Ala Tyr Ala Pro Phe Glu
545                 550                 555                 560

Phe Lys Tyr Pro Gly Tyr Lys Leu His Ser Val Ser Ala Tyr Gly Leu
                565                 570                 575

Ser Lys Ala Pro Asp Xaa Ala Asp Ser Val Met Phe Gly Phe Arg Pro
            580                 585                 590

Val Leu Leu Glu Asn Glu Ala Asn Gln Leu Leu Thr Asp Thr Ala Leu
        595                 600                 605

Gln Ile Pro Ala Glu Ile Gly Ile Thr Asp Val Val Pro Ala Phe Gly
    610                 615                 620

Arg Thr Glu Glu Pro Ile Asn Gly Gln Asp Ala Ile Xaa Ile Trp Glu
625                 630                 635                 640

Ser Phe Thr Ser Gly Phe Gly Phe Thr Tyr Thr Val Asp Ser Pro Gln
                645                 650                 655

Lys Gln Lys Tyr Lys Ile Ile Tyr Arg Ile Ala Asn Asn Leu Ser Ala
            660                 665                 670

Ser Thr Val Ser Leu Thr Tyr Asn Asn Gln Thr Phe Phe Thr Asp Ile
        675                 680                 685

Leu Asn Thr Ser Leu Asp Pro Asn Gly Val Arg Gly Asn Tyr Gly Ser
    690                 695                 700

Tyr Thr Leu Val Glu Gly Pro Ile Ile Glu Phe Ser Gln Gly Thr Asn
705                 710                 715                 720

Ile Phe Lys Leu Xaa Ser Gln Lys Gly Glu Phe Ala Ile Asp Ser Ile
                725                 730                 735

Ile Phe Ser Pro Val Xaa
            740
```

<210> SEQ ID NO 15
<211> LENGTH: 492
<212> TYPE: PRT
<213> ORGANISM: Bacillus thuringiensis
<220> FEATURE:
<221> NAME/KEY: MISC_FEATURE
<222> LOCATION: (1)..(1)
<223> OTHER INFORMATION: Xaa= isoleucine or methionine -continued
<220> FEATURE:
<221> NAME/KEY: MISC_FEATURE
<222> LOCATION: (139)..(139)
<223> OTHER INFORMATION: lysine or arginine
<220> FEATURE:
<221> NAME/KEY: MISC_FEATURE
<222> LOCATION: (194)..(194)
<223> OTHER INFORMATION: Xaa= serine or histidine
<220> FEATURE:
<221> NAME/KEY: MISC_FEATURE
<222> LOCATION: (195)..(195)
<223> OTHER INFORMATION: Xaa= glycine or serine
<220> FEATURE:
<221> NAME/KEY: MISC_FEATURE
<222> LOCATION: (196)..(196)
<223> OTHER INFORMATION: Xaa= glycine or proline
<220> FEATURE:
<221> NAME/KEY: MISC_FEATURE
<222> LOCATION: (216)..(216)
<223> OTHER INFORMATION: Xaa= glutamine or arginine
<220> FEATURE:
<221> NAME/KEY: MISC_FEATURE
<222> LOCATION: (231)..(231)
<223> OTHER INFORMATION: Xaa= tyrosine or tryptophan
<220> FEATURE:
<221> NAME/KEY: MISC_FEATURE
<222> LOCATION: (257)..(257)
<223> OTHER INFORMATION: Xaa= alanine or leucine
<220> FEATURE:
<221> NAME/KEY: MISC_FEATURE
<222> LOCATION: (260)..(260)
<223> OTHER INFORMATION: Xaa= glycine or histidine
<220> FEATURE:
<221> NAME/KEY: MISC_FEATURE
<222> LOCATION: (268)..(268)
<223> OTHER INFORMATION: Xaa= alanine or valine
<220> FEATURE:
<221> NAME/KEY: MISC_FEATURE
<222> LOCATION: (301)..(301)
<223> OTHER INFORMATION: Xaa= alanine or proline
<220> FEATURE:
<221> NAME/KEY: MISC_FEATURE
<222> LOCATION: (332)..(332)
<223> OTHER INFORMATION: Xaa=alanine or threonine
<220> FEATURE:
<221> NAME/KEY: MISC_FEATURE
<222> LOCATION: (387)..(387)
<223> OTHER INFORMATION: Xaa= arginine or isoleucine
<220> FEATURE:
<221> NAME/KEY: MISC_FEATURE
<222> LOCATION: (475)..(475)
<223> OTHER INFORMATION: Xaa= glycine or arginine
<220> FEATURE:
<221> NAME/KEY: MISC_FEATURE
<222> LOCATION: (492)..(492)
<223> OTHER INFORMATION: Xaa= valine or serine

<400> SEQUENCE: 15

```
Xaa Ala Glu Pro Pro Ser Thr Gly Val Ile Thr Gln Phe Arg Ile Leu
1               5                   10                  15

Asn Asp Asn Phe Ile Lys Tyr Ile Ala Lys Leu Gln Phe Ser Thr Asn
            20                  25                  30

Gln Ser Asp Leu Gln Tyr Pro Val Leu Thr Leu Pro Leu Arg Ala Gln
        35                  40                  45

Ala Cys Val Met His Leu Met Leu Leu Lys Asp Ala Thr Thr Ser Val
    50                  55                  60

Trp Gly Gln Gln Ile Asp Ser Gln Gln Leu Asn Gly Tyr Lys Ala Glu
65                  70                  75                  80

Leu Ile Arg Leu Ile Lys Val Tyr Thr Asn Asp Val Asn Thr Thr Tyr
                85                  90                  95

Asn Gln Gly Leu Glu Leu Glu Lys Ala Lys Pro Leu Asn Tyr Ser Asp
            100                 105                 110
```

-continued

```
Pro Glu Glu Tyr Leu Gln Ala Gly Arg Pro Asp Ile Ser Val Leu Arg
        115                 120                 125

Ser Asn Phe Lys Glu Val Met Lys Trp Asn Xaa Val Ala Lys Tyr Lys
    130                 135                 140

Arg Gly Met Ala Met Ser Ala Leu Ser Leu Ala Ala Leu Phe Pro Thr
145                 150                 155                 160

Phe Gly Pro Asn Tyr Pro Lys Gln Ala Leu Lys Val Val Gln Ser Arg
                165                 170                 175

Gln Ile Phe Ala Pro Val Ile Gly Ile Pro Gly Gly Ile Thr Ser Gln
            180                 185                 190

Asp Xaa Xaa Xaa Thr Phe Gly Ser Met Arg Phe Asp Val Lys Thr Tyr
        195                 200                 205

Asp Gln Ile Asp Ala Leu Arg Xaa Leu Met Glu Leu Tyr Ile Gln Pro
    210                 215                 220

Leu Lys Ser Ala Tyr Phe Xaa Ile Tyr Glu Ser Asp Trp Lys Val Arg
225                 230                 235                 240

Ala Thr Tyr Val Asn Asp Tyr Ile Gly Lys Arg Gly Ser Asn Thr Gly
                245                 250                 255

Xaa Ala Trp Xaa Met Trp Ser Ser Asp Pro Ser Xaa Ile Tyr Thr Ser
            260                 265                 270

Ala Leu Gly Ala Ala Gly Tyr Ala Pro Asn Val Val Gly Val Arg Tyr
        275                 280                 285

Ser His Gly Gly Ser Tyr Thr Lys Gly Met Ala Pro Xaa Asn Thr Asn
    290                 295                 300

Ala Tyr Ala Pro Phe Glu Phe Lys Tyr Pro Gly Tyr Lys Leu His Ser
305                 310                 315                 320

Val Ser Ala Tyr Gly Leu Ser Lys Ala Pro Asp Xaa Ala Asp Ser Val
                325                 330                 335

Met Phe Gly Phe Arg Pro Val Leu Leu Glu Asn Glu Ala Asn Gln Leu
            340                 345                 350

Leu Thr Asp Thr Ala Leu Gln Ile Pro Ala Glu Ile Gly Ile Thr Asp
        355                 360                 365

Val Val Pro Ala Phe Gly Arg Thr Glu Glu Pro Ile Asn Gly Gln Asp
    370                 375                 380

Ala Ile Xaa Ile Trp Glu Ser Phe Thr Ser Gly Phe Gly Phe Thr Tyr
385                 390                 395                 400

Thr Val Asp Ser Pro Gln Lys Gln Lys Tyr Lys Ile Ile Tyr Arg Ile
                405                 410                 415

Ala Asn Asn Leu Ser Ala Ser Thr Val Ser Leu Thr Tyr Asn Asn Gln
            420                 425                 430

Thr Phe Phe Thr Asp Ile Leu Asn Thr Ser Leu Asp Pro Asn Gly Val
        435                 440                 445

Arg Gly Asn Tyr Gly Ser Tyr Thr Leu Val Glu Gly Pro Ile Ile Glu
    450                 455                 460

Phe Ser Gln Gly Thr Asn Ile Phe Lys Leu Xaa Ser Gln Lys Gly Glu
465                 470                 475                 480

Phe Ala Ile Asp Ser Ile Ile Phe Ser Pro Val Xaa
                485                 490
```

<210> SEQ ID NO 16
<211> LENGTH: 3313
<212> TYPE: DNA
<213> ORGANISM: Bacillus thuringiensis -continued

<400> SEQUENCE: 16

```
aagagaatat tcctgtagat attatattta aatatagtct cactcctctt gcttatcata      60
ccgttgatac caatcatgta aaactcaaac atattggatt agtccctttt tcttcttccg     120
atcctaatct atacagcata caaggtgaat ttcaattttt ttatgaataa acaatactta     180
tgaaaaaact atttataagt atattaaagg acaacaaagt gagcataatg atggttttga     240
tgggaaagaa taataggctt tagtcaatag tggttcagtt aattattgat atattttgat     300
atttataata caaacatttc tcaaaaattc tccttgctta tgtccattta tacccaaaaa     360
agcgaggaca atgtatatat ttctctatct atcatagagt aaatatagac tgtatacatt     420
tttagtctta tctttgagtt tttatatatt ttaaagtttg tttgataaat tttcaggaaa     480
aaaagatctc aacgactttt gtatgtcggt tgtttactat gtgaaaggtg gagatattgt     540
ggacccattt tctaattatt ctgaacaaaa atacccagat tcaaataata accaagaact     600
aattacagaa tcctcttcat tttattcgga tactactaat gaaaatatga aaacttacca     660
tccaattgaa caagatattc tcaaatttgc aaatcaagaa tttcccgata attattatca     720
acattccgat gtttctaatt catatcaaaa tatgaaaaca gaaatcgtaa atacagattt     780
accctataat acaaataata taaatagtat gcgaaatact ctatgcagag atttacctcc     840
cgagactaac atgagcattt atgataattt acgatctact gttactgttc cttcattttc     900
taatcaattt gatcctataa aatttcttca cgatattgaa attgctatag aaactggatc     960
attttctgca ttaacgcaat ctaacatgaa tcaaggtggt actgatattg ctccaatgtt    1020
aatctctaca ttttttaaag ttgcaggtag tttacttcca tttcctctat catcattagg    1080
tgctttggct tccttttatg ttacagattc acaaacaggc gctatggcaa atttatggag    1140
acaaatggta gattatgttg aaaaaagaat tgattctaaa atattagatt atcataattt    1200
tattatggga gcagaactcg cagcattaaa tgcaagttta aaagaatacg cacgagtagt    1260
taaaattttt gaaaatgata tgaacagaat agctgaacca ccttcaactg gagttatcac    1320
tcaattcaga attcttaatg ataatttcat taaatatatt gcaaaattac aattctcaac    1380
aaatcaatca gatttacaat atcctgtcct aactttacca ttacgtgcac aagcatgtgt    1440
aatgcattta atgttattaa aagatgcaac gacttctgtg tggggacaac aaatagactc    1500
gcaacaatta aatgggtata aagcagaatt aatacgttta ataaaagtat atactaatga    1560
tgtaaacaca acgtataatc aagggctaga gctagaaaaa gctaaaccac taaattattc    1620
tgatcctgaa gaatatttac aagcaggacg tccagatata tctgtattac gcagtaactt    1680
taaagaggtt atgaagtgga ataaagtagc gaaatataaa cgtggaatgg ctatgagtgc    1740
tttatcatta gctgcattat ttccaacttt cggaccaaat tatccaaaac aagcattaaa    1800
agttgtgcaa tctagacaaa tttttgcacc tgtaattgga ataccaggcg gtataacaag    1860
tcaagatagt ggtcccactt ttggtagtat gagatttgat gtaaaaactt atgatcaaat    1920
tgatgcgtta cgacaactaa tggaattata tattcaacct ttaaaatctg cttacttttg    1980
gatatatgaa tcggattgga aagttcgtgc aacttatgtc aatgattata ttggtaaaag    2040
agggtcaaat acaggtgctg cttggcacat gtggtcaagt gatccttcag ccatatacac    2100
ttctgcacta ggagcagcag gatacgctcc taacgttgtt ggtgtaagat attcacatgg    2160
gggtagttac acaaaaggta tggcacccgc aaatactaat gcgtatgctc catttgaatt    2220
taaatatcct ggttataaac tacacagtgt tagtgcttat ggattaagta aagcacctga    2280
tgcagctgat tctgttatgt ttggatttag acctgtattg ttagaaaatg aagcaaatca    2340
```

-continued

```
attattaaca gatacagcat tgcaaattcc agcagaaata ggaataacag atgtcgtacc   2400
tgcatttggt agaacagaag aacctattaa tggtcaagat gcaataagaa tatgggaaag   2460
ttttacaagt ggatttggct ttacttatac tgttgattct ccacaaaaac aaaaatataa   2520
aatcatttat agaattgcaa ataacttaag cgcttctaca gtttctttaa cctataataa   2580
tcaaacattt ttcactgata ttttaaatac ttcattagat ccaaatggag taagaggaaa   2640
ttatggttct tatacacttg tagaaggtcc tattattgaa ttttctcaag gaactaatat   2700
ctttaaacta ggatcacaaa aaggagaatt cgctatagat tccattattt ttagtcctgt   2760
tgtttaatag tgtagtacca ttagacccag acccatggtt tccagtccag aatattcccc   2820
agatttcata gtatgcttcg atcccgcatg ttttatgtac aaacacatcc tttttagata   2880
gcattccaat tatagggatg ctcttttttt gatttctggc ctatccttct catttcatag   2940
atttttaatt agtacccttt acaaaaagta aacccaccat cttcgaacaa atctttgatt   3000
tctattttta agaataatca atctgttgaa caatttataa ttcttttgaa gagaatttca   3060
ttttatttgt tcgcttaagt tgataggcat gtggttctac ccctaataag tgtcacagaa   3120
cactaattct aagacattta tcgtaaaaaa atagtaaatt catacaatac agttaaactt   3180
tcctcagtag ctcacgtttt tcgatttcgg gtgtttttac tcatttcccc ctttgttttt   3240
aggagagagt gctggctggg ggtttggggg ctagccccca agaacttaac gtaactgaat   3300
atggaataag ctt                                                       3313
```

<210> SEQ ID NO 17
<211> LENGTH: 2172
<212> TYPE: DNA
<213> ORGANISM: Bacillus thuringiensis

<400> SEQUENCE: 17

```
gtggacccgt tttctaatta ttctgaacaa aaatacccag attcaaataa taaccaagaa     60
ctaattacaa aatcctcttc attttattcg gatactacta atgaaaatgc aaaaaattac    120
cacccaattg aacaagatat tctcaaattt acaaatcaag aattttccga taatcattat    180
caacattccg atgtttcaaa tgatataaat agtatgcgaa atactctatg caaagattta    240
cctcctgaga ctaacatgag catttatgat aatttacgat ctactgttac tgttccttca    300
ttttctaatc aatttgatcc tataaaattt cttcacgata ttgaaattgc tatacaaact    360
ggatcatttt ctgcattaac gcaatctaac atgaatcaag gtggtactga tattaatcca    420
atgttaatct ctacattttt taaagttgca agtagtttac ttccatttcc tctatcatca    480
ttaggtgctt tagcttcctt ttatgttaca gattcacaaa caggcgctat ggcaaattta    540
tggagacaaa tggtagatta tgttgaaaaa agaattgatt ctaaaatatt agattatcat    600
aattttatta tgggagcaga actcgcagca ttaaatgcaa gtttaaaaga atacgcacga    660
gtagttaaaa tttttgaaaa tgatatgaac agaatggctg aaccaccttc aactggagtt    720
atcactcaat tcagaattct taatgataat ttcattaaat acattgcaaa attacaattc    780
tcaacaaatc aatcagattt acaatatcct gtcctaactt taccattacg tgcacaagca    840
tgtgtaatgc atttaatgtt attaaaagat gcaacgactt ctgtgtgggg acaacaaata    900
gactcgcaac aattaaatgg gtataaagca gaattaatac gtttaataaa agtatatact    960
aatgatgtaa acacaacgta taatcaaggg ctagagctag aaaaagctaa accactaaat   1020
tattctgatc ctgaagaata tttacaagca gggcgtccag atatatctgt attacgcagt   1080
```

-continued

```
aactttaaag aggttatgaa gtggaataga gtagcgaaat ataaacgtgg aatggctatg   1140

agtgctttat cattagctgc attatttcca actttcggac caaattatcc aaaacaagca   1200

ttaaaagttg tgcaatctag acaaattttt gcacctgtaa ttggaatacc aggcggtata   1260

acaagtcaag atcattctgg cacttttggt agtatgagat ttgatgtaaa aacttatgat   1320

caaattgatg cgttacgacg actaatggaa ttatatattc aacctttaaa atctgcctac   1380

ttctatatat atgaatcgga ttggaaagtt cgtgcaactt atgtcaatga ctatattggt   1440

aaaagagggt ctaatacagg tcttgcctgg ggaatgtggt caagtgatcc ttcagtcata   1500

tacacttctg cactaggagc agcaggatac gctcctaacg ttgttggtgt aagatattca   1560

catgggggta gttacacaaa aggtatggca cccccaaata ctaatgcgta tgctccattt   1620

gaatttaaat atcctggtta taaactacac agtgttagtg cttatggatt aagtaaagca   1680

cctgatacag ctgattctgt tatgtttgga tttagacctg tattgttaga aaatgaagca   1740

aatcaattat taacagatac agcattgcaa attccagcag aaataggaat aacagatgtc   1800

gtacctgcat ttggtagaac agaagaacct attaatggtc aagatgcaat aataatatgg   1860

gaaagtttta caagtggatt tggctttact tatactgttg attctccaca aaaacaaaaa   1920

tataaaatca tttatagaat tgcaaataac ttaagcgctt ctacagtttc tttaacctat   1980

aataatcaaa catttttcac tgatatttta aatacttcat tagatccaaa tggagtaaga   2040

ggaaattatg gttcttatac acttgtagaa ggtcctatta ttgaattttc tcaaggaact   2100

aatatcttta aactaagatc acaaaaagga gaattcgcta tagattccat tatttttagt   2160

cctgtttcat aa                                                       2172


<210> SEQ ID NO 18
<211> LENGTH: 723
<212> TYPE: PRT
<213> ORGANISM: Bacillus thuringiensis

<400> SEQUENCE: 18

Met Asp Pro Phe Ser Asn Tyr Ser Glu Gln Lys Tyr Pro Asp Ser Asn
1               5                   10                  15

Asn Asn Gln Glu Leu Ile Thr Lys Ser Ser Ser Phe Tyr Ser Asp Thr
            20                  25                  30

Thr Asn Glu Asn Ala Lys Asn Tyr His Pro Ile Glu Gln Asp Ile Leu
        35                  40                  45

Lys Phe Thr Asn Gln Glu Phe Ser Asp Asn His Tyr Gln His Ser Asp
    50                  55                  60

Val Ser Asn Asp Ile Asn Ser Met Arg Asn Thr Leu Cys Lys Asp Leu
65                  70                  75                  80

Pro Pro Glu Thr Asn Met Ser Ile Tyr Asp Asn Leu Arg Ser Thr Val
                85                  90                  95

Thr Val Pro Ser Phe Ser Asn Gln Phe Asp Pro Ile Lys Phe Leu His
            100                 105                 110

Asp Ile Glu Ile Ala Ile Gln Thr Gly Ser Phe Ser Ala Leu Thr Gln
        115                 120                 125

Ser Asn Met Asn Gln Gly Gly Thr Asp Ile Asn Pro Met Leu Ile Ser
    130                 135                 140

Thr Phe Phe Lys Val Ala Ser Ser Leu Leu Pro Phe Pro Leu Ser Ser
145                 150                 155                 160

Leu Gly Ala Leu Ala Ser Phe Tyr Val Thr Asp Ser Gln Thr Gly Ala
                165                 170                 175
```

-continued

```
Met Ala Asn Leu Trp Arg Gln Met Val Asp Tyr Val Glu Lys Arg Ile
            180                 185                 190

Asp Ser Lys Ile Leu Asp Tyr His Asn Phe Ile Met Gly Ala Glu Leu
        195                 200                 205

Ala Ala Leu Asn Ala Ser Leu Lys Glu Tyr Ala Arg Val Val Lys Ile
    210                 215                 220

Phe Glu Asn Asp Met Asn Arg Met Ala Glu Pro Pro Ser Thr Gly Val
225                 230                 235                 240

Ile Thr Gln Phe Arg Ile Leu Asn Asp Asn Phe Ile Lys Tyr Ile Ala
                245                 250                 255

Lys Leu Gln Phe Ser Thr Asn Gln Ser Asp Leu Gln Tyr Pro Val Leu
            260                 265                 270

Thr Leu Pro Leu Arg Ala Gln Ala Cys Val Met His Leu Met Leu Leu
        275                 280                 285

Lys Asp Ala Thr Thr Ser Val Trp Gly Gln Gln Ile Asp Ser Gln Gln
    290                 295                 300

Leu Asn Gly Tyr Lys Ala Glu Leu Ile Arg Leu Ile Lys Val Tyr Thr
305                 310                 315                 320

Asn Asp Val Asn Thr Thr Tyr Asn Gln Gly Leu Glu Leu Glu Lys Ala
                325                 330                 335

Lys Pro Leu Asn Tyr Ser Asp Pro Glu Glu Tyr Leu Gln Ala Gly Arg
            340                 345                 350

Pro Asp Ile Ser Val Leu Arg Ser Asn Phe Lys Glu Val Met Lys Trp
        355                 360                 365

Asn Arg Val Ala Lys Tyr Lys Arg Gly Met Ala Met Ser Ala Leu Ser
    370                 375                 380

Leu Ala Ala Leu Phe Pro Thr Phe Gly Pro Asn Tyr Pro Lys Gln Ala
385                 390                 395                 400

Leu Lys Val Val Gln Ser Arg Gln Ile Phe Ala Pro Val Ile Gly Ile
                405                 410                 415

Pro Gly Gly Ile Thr Ser Gln Asp His Ser Gly Thr Phe Gly Ser Met
            420                 425                 430

Arg Phe Asp Val Lys Thr Tyr Asp Gln Ile Asp Ala Leu Arg Arg Leu
        435                 440                 445

Met Glu Leu Tyr Ile Gln Pro Leu Lys Ser Ala Tyr Phe Tyr Ile Tyr
    450                 455                 460

Glu Ser Asp Trp Lys Val Arg Ala Thr Tyr Val Asn Asp Tyr Ile Gly
465                 470                 475                 480

Lys Arg Gly Ser Asn Thr Gly Leu Ala Trp Gly Met Trp Ser Ser Asp
                485                 490                 495

Pro Ser Val Ile Tyr Thr Ser Ala Leu Gly Ala Ala Gly Tyr Ala Pro
            500                 505                 510

Asn Val Val Gly Val Arg Tyr Ser His Gly Gly Ser Tyr Thr Lys Gly
        515                 520                 525

Met Ala Pro Pro Asn Thr Asn Ala Tyr Ala Pro Phe Glu Phe Lys Tyr
    530                 535                 540

Pro Gly Tyr Lys Leu His Ser Val Ser Ala Tyr Gly Leu Ser Lys Ala
545                 550                 555                 560

Pro Asp Thr Ala Asp Ser Val Met Phe Gly Phe Arg Pro Val Leu Leu
                565                 570                 575

Glu Asn Glu Ala Asn Gln Leu Leu Thr Asp Thr Ala Leu Gln Ile Pro
            580                 585                 590

Ala Glu Ile Gly Ile Thr Asp Val Val Pro Ala Phe Gly Arg Thr Glu
```

-continued

```
        595                 600                 605

Glu Pro Ile Asn Gly Gln Asp Ala Ile Ile Ile Trp Glu Ser Phe Thr
    610                 615                 620

Ser Gly Phe Gly Phe Thr Tyr Thr Val Asp Ser Pro Gln Lys Gln Lys
625                 630                 635                 640

Tyr Lys Ile Ile Tyr Arg Ile Ala Asn Asn Leu Ser Ala Ser Thr Val
                645                 650                 655

Ser Leu Thr Tyr Asn Asn Gln Thr Phe Phe Thr Asp Ile Leu Asn Thr
            660                 665                 670

Ser Leu Asp Pro Asn Gly Val Arg Gly Asn Tyr Gly Ser Tyr Thr Leu
        675                 680                 685

Val Glu Gly Pro Ile Ile Glu Phe Ser Gln Gly Thr Asn Ile Phe Lys
    690                 695                 700

Leu Arg Ser Gln Lys Gly Glu Phe Ala Ile Asp Ser Ile Ile Phe Ser
705                 710                 715                 720

Pro Val Ser
```